US009023602B2

(12) United States Patent
Helder et al.

(10) Patent No.: US 9,023,602 B2
(45) Date of Patent: May 5, 2015

(54) METHOD FOR DETECTING CYST NEMATODES

(75) Inventors: Johannes Helder, Wageningen (NL); Gerrit Karssen, Bennekom (NL); Sven Johannes Josephus van den Elsen, Boekel (NL); Martijn Hermanus Maria Holterman, Wageningen (NL); Paulus Jacques Willem Mooijman, Wageningen (NL); Roel Victor Staps, Nijmegen (NL); Renske Landeweert, Oosterbeek (NL); Henri Hekman, Oosterbeek (NL); Jaap Bakker, Wageningen (NL)

(73) Assignees: Wageningen Universiteit, Wageningen (NL); Tree of Knowledge Patents B.V., Wageningen (NL)

( * ) Notice: Subject to any disclaimer, the term of this patent is extended or adjusted under 35 U.S.C. 154(b) by 746 days.

(21) Appl. No.: 12/520,927

(22) PCT Filed: Dec. 21, 2007

(86) PCT No.: PCT/NL2007/050700
§ 371 (c)(1),
(2), (4) Date: Oct. 1, 2009

(87) PCT Pub. No.: WO2008/079012
PCT Pub. Date: Jul. 3, 2008

(65) Prior Publication Data
US 2010/0062439 A1    Mar. 11, 2010

(30) Foreign Application Priority Data

Dec. 27, 2006 (EP) .................... 06077326

(51) Int. Cl.
C12Q 1/68    (2006.01)
C12P 19/34    (2006.01)

(52) U.S. Cl.
CPC .................... C12Q 1/6888 (2013.01)

(58) Field of Classification Search
None
See application file for complete search history.

(56) References Cited

U.S. PATENT DOCUMENTS 4,683,195 A    7/1987 Mullis et al.
4,683,202 A    7/1987 Mullis
4,800,159 A    1/1989 Mullis et al.
5,270,184 A    12/1993 Walker et al.
5,455,166 A    10/1995 Walker
5,719,028 A    2/1998 Dahlberg et al.
5,871,921 A    2/1999 Landegren et al.
5,942,391 A    8/1999 Zhang et al.
2010/0064391 A1    3/2010 Vincken et al.
2010/0081133 A1    4/2010 Helder et al.

FOREIGN PATENT DOCUMENTS

EP    0320308    11/1993
WO    WO 00/73422    12/2000
WO    WO 01/25449    4/2001
WO    WO 2004/090164    10/2004
WO    WO 2008/007959    1/2008
WO    WO 2008/033018    3/2008

OTHER PUBLICATIONS

Holterman et al. Phylum-wide analysis of SSU rDNA reveals deep phylogenetic relationships among nematodes and accelerated evolution toward crown clades. Mol. Biol Evol. (2006) vol. 23, No. 9, pp. 1792-1800.*
Castillo et al. (2003) "A New Root-Knot Nematode, *Meloidogyne baetica* n. sp. (Nematoda: Heteroderidae), Parasitizing Wild Olive in Southern Spain" Nematology 93(9): 1093-1102.
Chitwood et al. (2003) "Research on Plant-Parasitic Nematode Biology Conducted by the United States Department of Agriculture-Agricultural Research Service" Pest Management Science 59:748-753.
Ferris et al. (1993) "Variation in Spacer Ribosomal DNA in Some Cyst—Forming Species of Plant Parasitic Nematodes" Fundam. Appl. Nematol. 16(2): 177-184.
Ferris et al. (1995) "Ribosomal DNA Comparisons of *Globodera* from Two Continents" Journal of Nematology 27(3): 273-283.
Ferris et al. (2004) "Phylogenetic Relationships Among Selected Heteroderoidea Based on 18S and ITS Ribosomal DNA" Journal of Nematology 36(3): 202-206.
Marshall et al. (1993) "Detecting the Presence and Distribution of *Globodera rostochiensis* and *G. Pallida* Mixed Populations in New Zealand Using DNA Probes" 21:219-223.
Pylypenko et al. (2005) "Identification of *Globodera rostochiensis* and *G. Pallida* in the Ukraine by PCR" European Journal of Plant Pathology 111:39-46.

(Continued)

*Primary Examiner* — Kenneth R. Horlick
*Assistant Examiner* — David Thomas
(74) *Attorney, Agent, or Firm* — Swanson & Bratschun, L.L.C.

(57) ABSTRACT

The present invention relates to a method for determining the presence of a cyst nematode in a sample comprising the steps of: providing a pair of bidirectional oligonucleotide primers or an oligonucleotide probe that hybridizes specifically, under stringent hybridization conditions, to a nucleic acid sequence encoding the SSU rRNA or LSU rRNA, or the complement or transcript thereof, of a sub genus-cluster of nematodes, said subgenus-cluster comprising cyst nematodes belonging to at least one species of nematode, and wherein said primers or probe do not hybridize to a nucleic acid sequence encoding the LSU rRNA, or the complement or transcript thereof, of cyst nematodes not part of said subgenus-cluster of cyst nematodes; providing a sample in which the presence of the cyst nematode is to be detected, and performing a nucleic acid detection assay on said sample using said pair of bidirectional oligonucleotide primers or said oligonucleotide probe.

12 Claims, 20 Drawing Sheets

(56) References Cited

OTHER PUBLICATIONS

Figure 1:
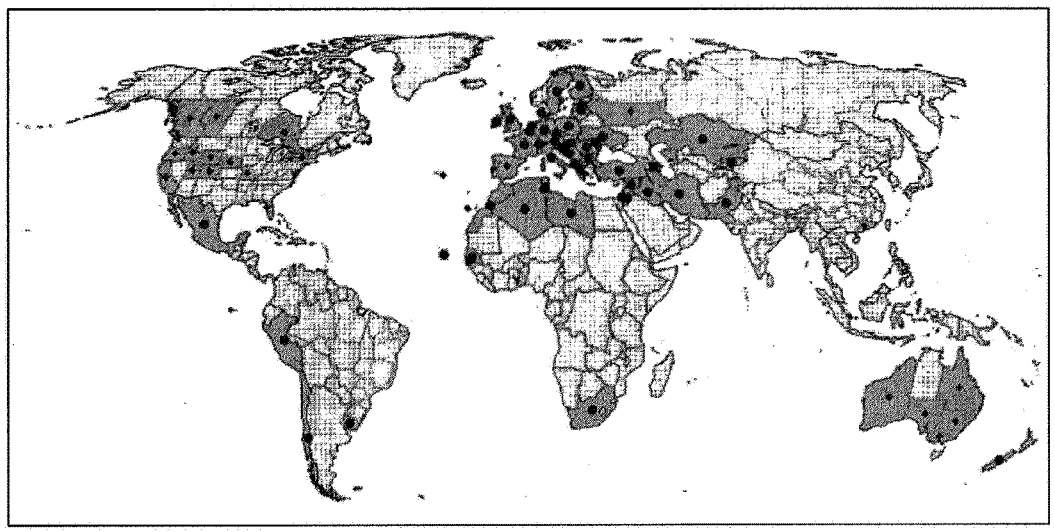

Reid and Pickup (2005) "Molecular Characterization of a Morphologically Unusual Potato Cyst Nematode" OEPP/EPPO Bulletin 35:69-72.
Subbotin et al. (2001) "A Rapid Method for the Identification of the Soybean Cyst Nematode *Heterodera glycines* Using Duplex PCR" Nematology 3(4): 365-371.
Subbotin et al. (2002) "Molecular Phylogenetics of the Cyst-Forming Nematodes (Tylenchida: Heteroderidae)" Nematology 4(2): 181-182.
Subbotin et al. (2003) "Molecular and Morphological Characterisation of the *Heterodera avenae* Species Complex (Tylenchida: Heteroderidae)" Nematology 5(4): 515-538.
Szalanski et al. (1997) "Identification of Cyst Nematodes of Agronomic and Regulatory Concern with PCT-RFLP of ITS1" Journal of Nematology 29(3): 255-267.
Chen, et al. (2003) J of Nematology 35(4):404-410, "Nucleotide Substitution Patterning within the Meloidogyne rDNA D3 Region and Its Evolutionary Implications".
Database EMBL Online (Sep. 30, 2004). Laboratory of Nematology, Wageningen University, Department of Plant Sciences, The Netherlands. "*Meloidogyne chitwoodi* strain MeloChi8 4 902+903 18S ribosomal RNA gene, partial sequence," Database accession No. AY593889.
Database EMBL Online (Jul. 2, 2002). Nematology, University of California, Riverside, CA, USA. "*Meloidogyne chitwoodi* strain Mchi 28S large subunit ribosomal RNA gene, partial sequence," Database accession No. AF435802.
De Ley, et al. (2002) J of Nematology 34:319-327, "Phylogenetic Analyses of *Meloidogyne* Small Subunit rDNA".
Ji, et al. (2003) Plant Molecular Biology 51:789-801, "Microbial starch-binding domains as a tool for targeting proteins to granules during starch biosynthesis".
Kok-Jacon (2003) J of Plant Physiology 160:765-777, "Towards a more versatile glucan biosynthesis in plants".
Kok-Jacon, et al. (2005) Plant Biotechnology Journal 3:341-351, "Mutan produced in potato amylopasts adheres to starch granules".
Potocki-Veronese, et al. (2005) Biomacromolecules 6:1000-1011, "Amylose Synthesized in Vitro by Amylosucrase Morphology, Structure, and Properties".
Skantar and Carta (2005) Nematology 7(2):285-293, "Multiple displacement amplification (MDA) of total genomic DNA from *Meloidogyne* spp. And comparision to crude DNA extracts in PCF of ITS1, 28S D2-D3 rDNA and Hsp90".
Tenente (2004) Nematropica 34:1-12, "Sequence analysis of the D2/D3 Region of the Large Subunit rDNA from Different *Meloidogyne* Isolates".
Tigano, et al. (2005) Nematology 7:851-862, "Phylogeny of Meloidogyne spp. Based on 18S rDNA and the intergenic region of mitochondrial DNA sequences".
Bonetta et al. "Prime time for real-time PCR" (2005) Nature Methods 2(4):305.

\* cited by examiner

```
                          10         20         30         40         50         60         70         80
                 ....|....|....|....|....|....|....|....|....|....|....|....|....|....|....|....|
Consensus Clade 1-6   AAGAAACTAACGAGGATTCCCGKAGTAACGGCGAGTGAGTGAACTGGGAAGAGTCCAGCGCTGAATCRCHKCTCCTCTGGGGWY 90        100        110        120        130        140        150        160
                 ....|....|....|....|....|....|....|....|....|....|....|....|....|....|....|....|
Consensus Clade 1-6   GYGAGGTGTAGCGTAYAGACCGCTRAGCTTGGCCYGCTBGTTCAAGTTTCCCTTGAYCGGGGCTCCAGAGAAGGT 170        180        190        200        210        220        230        240
                 ....|....|....|....|....|....|....|....|....|....|....|....|....|....|....|....|
Consensus Clade 1-6   GCAAGACCTGTCCAACKRGYGGTYGCCTAYYCATCTTYRCGTGT

```
                  810        820        830        840        850        860        870        880
                 ....|....|....|....|....|....|....|....|....|....|....|....|....|....|....|....|
Consensus Clade 1-6  CYAARGGCGYAATGAAAGTRAAGGYHRTYCTTRCGGARCTGATGTGTGATCYCBDGCACYNCCGGTGTBVGGGCGCAACA 890        900        910        920        930        940        950        960
                 ....|....|....|....|....|....|....|....|....|....|....|....|....|....|....|....|
Consensus Clade 1-6  TAGTCCCGTYYTCDATCGCWTGCGATGGGGCGGAGAC Clade 1 - DNA sequence signatures From position 59 onwards      (SEQ ID No.2)
   gaatcGcaGCTcctCtggGGTTgCgaggtgtagc From position 90 onwards      (SEQ ID No.3)
   agcgtaTaGACcgTGAGcttggG From position 160 onwards     (SEQ ID No.4)
   tgcaagAcctgtCcaAcTGgCggYgcctaccc From position 185 onwards     (SEQ ID No.5)
   gcctaCcCatcttTAcgtgtcttg From position 231 onwards     (SEQ ID No.6)
   agcccaaaTCAggtggtaaactt From position 419 onwards     (SEQ ID No.7)
   gggCtGCTAGCCtccagac From position 437 onwards     (SEQ ID No.8)
   actggggttKgCtgtccttc From position 464 onwards     (SEQ ID No.9)
   gTggcGAatggGgcatttgcagg From position 504 onwards     (SEQ ID No.10)
   ctcggAgTagctgCGtgagctC From position 520 onwards     (SEQ ID No.11)
   gaGctCggTCttgaggccagcC From position 552 onwards     (SEQ ID No.12)
   tctggtacccgGATCggggKagt From position 583 onwards     (SEQ ID No.13)
   ctctgggtgAATtgtgcaa From position 693 onwards     (SEQ ID No.14)
   gctctcaGttgtgcgttctcggtg From position 820 onwards     (SEQ ID No.15)
   gaaggcttcttAcggagctgat

Figure 13

Clade 2 - DNA sequence signatures

From position 440 onwards           (SEQ ID No.16)
    GgGgYTggTTGTcCTtctgt

From position 558 onwards           (SEQ ID No.17)
    acccggGTCgggggaGtgCtgtttGCtctgggtg

Figure 14

Clade 3 - DNA sequence signatures

From position 42 onwards          (SEQ ID No.18)
   gggaagagtccagcgctgaatcGcATctccYctggggATgTgagg From position 98 onwards          (SEQ ID No.19)
   gaccgTAagcttggGttggccc
       **
From position 174 onwards         (SEQ ID No.20)
   aactAgYggTgcctacTcatcttTGcgtg From position 398 onwards         (SEQ ID No.21)
   aCccgtCtgttGTtgGAcgttgggcttCCTGc From position 440 onwards         (SEQ ID No.22)
   ggggtCggTtgtCTTtctgttc From position 496 onwards         (SEQ ID No.23)
   ctgagaTgctcggGGTagctgcGtgaActCggCTttgagg From position 558 onwards         (SEQ ID No.24)
   acccggGTcgggggaAtgctgtttACtctgggtgagAgtgtgcaatggtt From position 660 onwards         (SEQ ID No.25)
   acacgtAccagcaATCagttcgg From position 718 onwards         (SEQ ID No.26)
   aaaagCCggtTatctgtCcgaccc

Figure 15

Clade 4 - DNA sequence signatures

From position 364 onwards    (SEQ ID No.27)
   aaacggaCagagCCgGcgtat

From position 407 onwards    (SEQ ID No.28)
   ttGTtgGGcAttgggctGYCAgCTtccagactgggGCggYGgtTcattWgtCYTgYggcTCatggGgcatttgca From position 587 onwards    (SEQ ID No.29)
   gggtGTATGTGTGTGAtggTCAcgggtT From position 662 onwards    (SEQ ID No.30)
   acgtAccAGcaGTTagttcggtccGgTtcgggctctcattgcat From position 725 onwards    (SEQ ID No.31)
   ggtTatctGtTTgacccgtcttg From position 815 onwards    (SEQ ID No.32)
   aaagtAaaggTGtCcttGCggaActgatgtgTgatcCcGAgcacTTcggtgYGAgggcgcaAcatagT

Figure 16

Clade 5 - DNA sequence signatures

From position 109           (SEQ ID No.33)
   tgagcttGgAYtggccY

From position 558 onwards (SEQ ID No.34)
acccgggcTgTgggagtgCt

Figure 17

Clade 6 - DNA sequence signatures

From position 135 onwards      (SEQ ID No.35)
    cccttgaTCggggCtccaGag

From position 403 onwards      (SEQ ID No.36)
    tgtgCtYTtgggcgtttggATT

From position 584 onwards      (SEQ ID No.37)
    tctgggtgCtgAgtGGtgtgca

From position 848 onwards      (SEQ ID No.38)
    gatcCcGTgcaccAcggtg

Figure 18

SPECIES SPECIFIC SNPs

Clade 1; Heterodera schachtii:
From position 172 onwards      (SEQ ID No.39)
CCAACTGGCGGTGCCTACCCATCTTTACGTGTCTTGG

Clade 1; Heterodera glycines:
From position 435 onwards      (SEQ ID No.40)
AGACTGGGGTTTGCTGTCCTTCTGTTC From position 613 onwards      (SEQ ID No.41)
TCGGGTCCGTGTTGACTCGAGCTGGGGG

Clade 1; Heterodera schachtii and/or Heterodera glycines:
From position 800 onwards      (SEQ ID No.42)
CCCAAAGGCGCAATGAAAGTGAA

Clade 1; Heterodera trifolii and/or Heterodera betae:
From position 172 onwards      (SEQ ID No.43)
CCAACTGGCGGCGCCTACCCATCTTTACGTGTCTTGG

Figure 19

SPECIES SPECIFIC SNPs

Clade 2; Heterodera zeae
From position 376 onwards      (SEQ ID No.44)
CTGGCGTATCTGGCTTGCATTCACCCGTTTGTTGTTGCGCGTTGGGC From position 444 onwards      (SEQ ID No.45)
CTGGTTGTCCTTCTGTGCGGCGGCTGATGGGGCATTTGCAGGCGGAGTGCGCCGAGA From position 584 onwards      (SEQ ID No.46)
TCTGGGTGCACAGCGCGGTGGTT

Figure 20

SPECIES SPECIFIC SNPs

Clade 3; Heterodera avenae
From position 435 onwards (SEQ ID No.47)
AGACTGGGGTCGGTTGTCTTTCTGTTC (cross reactivity with Heterodera aucklandica)

From position 462 onwards    (SEQ ID No.48)
AGCGGCTGATGGGGCATT (cross reactivity with Heterodera aucklandica)

From position 481 onwards    (SEQ ID No.49)
TGCAGGCGGAGTGCGCTGAGA (cross reactivity with Heterodera mani)

(471 or 502) combined with 527 = specific

Figure 21

SPECIES SPECIFIC SNPs

Clade 4; Heterodera goettingiana
From position 435 onwards     (SEQ ID No.50)
AGACTGGGGCGGCGGTTCATTWGTCYTGYGGCT From position 540 onwards     (SEQ ID No.51)
CCTTCGGACTGGTACCCGGGCTGG From position 608 onwards     (SEQ ID No.52)
TGGTCACGGGTTCGTGCTTGGTCGAGCTGGCGG

Figure 22

SPECIES SPECIFIC SNPs

Clade 5; Globodera pallida
From position 148 onwards        (SEQ ID No.53)
CTCCAGAGAAGGTRCAAGACCTGTCCAACGGGTGGTTGCC From position 445 onwards        (SEQ ID No.54)
TGGTGTTCMTTCTGCTCAGGGGGCT From position 502 onwards        (SEQ ID No.55)
TGCTCGGGACAGCTGCATGAGCTTGGCTT From position 629 onwards        (SEQ ID No.56)
TTGAGCTGGTGGTTGGTGGCGGTC From position 653 onwards        (SEQ ID No.57)
GCGTGCGACACGTGCCGGCRGTCAGT

Clade 5; Globodera tabacum
From position 398 onwards        (SEQ ID No.58)
ATCCGTGTGTTCTTGGACGTTTGGATTGCCACTCTCC From position 856 onwards        (SEQ ID No.59)
GCACTCCGGTGTGCGGGCGCAACATAGTCCCGTCC

Clade 5; Globodera rostochiensis
From position 113 onwards        (SEQ ID No.60)
ATTGGCCTGCTTGTTCAAGTTTCCCTTG

Figure 23

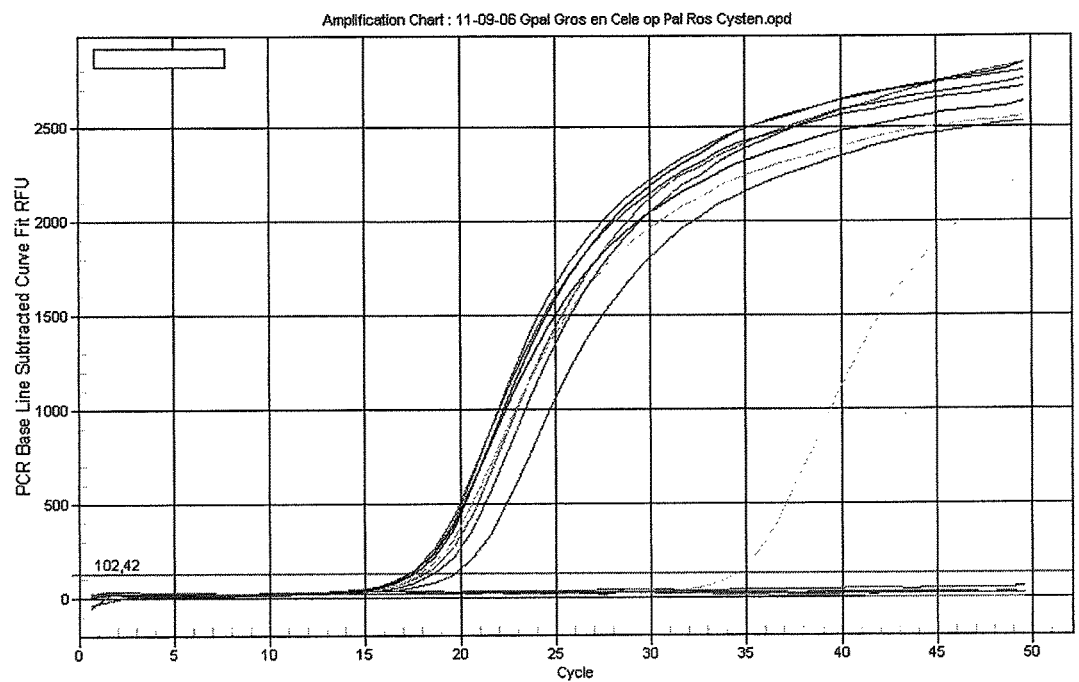
A
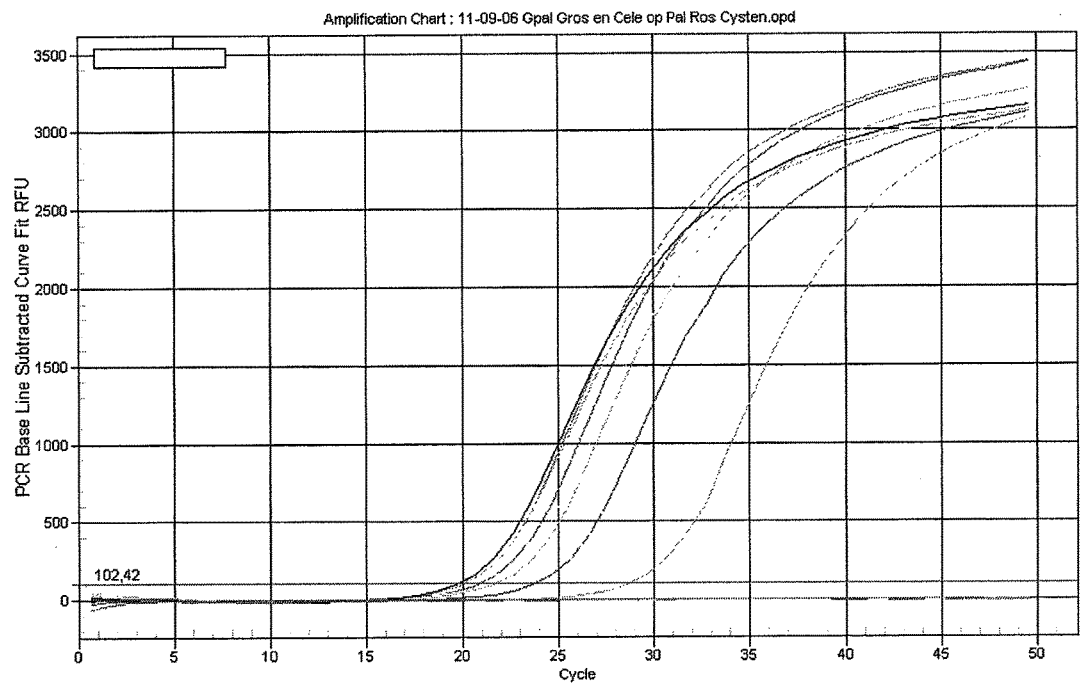
B
Figure 24

SEQUENCE LISTING

<160> NUMBER OF SEQ ID NOS: 64

<210> SEQ ID NO 1
<211> LENGTH: 1086
<212> TYPE: DNA
<213> ORGANISM: Artificial
<220> FEATURE:
<223> OTHER INFORMATION: consensus sequentie LSU-rDNA
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (470)..(470)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t

<400> SEQUENCE: 1

```
aagaaactaa cgaggattcc cgkagtaacg gcgagtgaac tgggaagagt ccagcgctga      60
atcrchkctc ctctggggwy gygaggtgta gcgtayagac cgctragctt ggrttggccy     120
gctbgttcaa gtttcccttg aycggggctc cagagaaggt gcaagacctg tccaackrgy     180
ggtygcctay ycatcttyrc gtgtcttgga gtcgggttgt ttgggatcgc agcccaaaky     240
```

-continued

```
aggtggtaaa cttcatctaa gactraatac ggccacgagt ccgatagcga acaagtaccg    300
tgagggaaag ttgcaaagca ctttgaagag agagttaaag aggacgtgaa accgatgagr    360
tggaaacgga cagagcyggc gtatctggtc tgcattcayc cgtbtgytby tgbrcrttkg    420
ghttkcywny ytccagactg ggryyggykk tyhwtytgyb cdggbggckn atggrgcatt    480
tgcaggcgga gtgcgctgag atgctcggrr yagctgcrtg arctyggyyt tgaggccagc    540
cyttcacggg gtctggtacc cggryygkgg gartgytgtt trytctgggt gcthvhgtgg    600
tgtgyratgg yhwcgggtyc gtgytggbty gagctgrbkg tyggtggcgg tcgcdtgcga    660
cacgtrccrg caryhagttc ggtccdgytc gggctctcad ttgyrygttc tcggtgtaaa    720
agccggtyat ctgtyygacc cgtcttgaaa cacggaccca aggagtttag cgtrtgcgcr    780
agtcattggg wgttsaaaac cyaarggcgy aatgaaagtr aaggyhrtyc ttrcggarct    840
gatgtgtgat cycbdgcacy nccggtgtbv gggcgcaaca tagtcccgty ytcdatcgcw    900
tgcgatgggg cggagacagm gcgtaygcgc tgagacccga aagatggtga atctattcct    960
gagcaggatg aagccagagg aaactctggt ggaagtccga agcgattctg acgtgcaaat   1020
cgatcgtctg acttgggtat aggggcgaaa gactaatcga accatctagt agctggttcc   1080
ctccga                                                              1086

<210> SEQ ID NO 2
<211> LENGTH: 34
<212> TYPE: DNA
<213> ORGANISM: Artificial
<220> FEATURE:
<223> OTHER INFORMATION: target clade 1

<400> SEQUENCE: 2
gaatcgcagc tcctctgggg ttgcgaggtg tagc                                 34

<210> SEQ ID NO 3
<211> LENGTH: 23
<212> TYPE: DNA
<213> ORGANISM: Artificial
<220> FEATURE:
<223> OTHER INFORMATION: target clade 1

<400> SEQUENCE: 3
agcgtataga ccgtgagctt ggg                                             23

<210> SEQ ID NO 4
<211> LENGTH: 32
<212> TYPE: DNA
<213> ORGANISM: Artificial
<220> FEATURE:
<223> OTHER INFORMATION: target clade 1

<400> SEQUENCE: 4
tgcaagacct gtccaactgg cggygcctac cc                                   32

<210> SEQ ID NO 5
<211> LENGTH: 24
<212> TYPE: DNA
<213> ORGANISM: Artificial
<220> FEATURE:
<223> OTHER INFORMATION: target clade 1

<400> SEQUENCE: 5
gcctacccat ctttacgtgt cttg                                            24
```

```
<210> SEQ ID NO 6
<211> LENGTH: 23
<212> TYPE: DNA
<213> ORGANISM: Artificial
<220> FEATURE:
<223> OTHER INFORMATION: target clade 1

<400> SEQUENCE: 6
agcccaaatc aggtggtaaa ctt                                              23

<210> SEQ ID NO 7
<211> LENGTH: 19
<212> TYPE: DNA
<213> ORGANISM: Artificial
<220> FEATURE:
<223> OTHER INFORMATION: target clade 1

<400> SEQUENCE: 7
gggctgctag cctccagac                                                   19

<210> SEQ ID NO 8
<211> LENGTH: 20
<212> TYPE: DNA
<213> ORGANISM: Artificial
<220> FEATURE:
<223> OTHER INFORMATION: target clade 1

<400> SEQUENCE: 8
actggggttk gctgtccttc                                                  20

<210> SEQ ID NO 9
<211> LENGTH: 23
<212> TYPE: DNA
<213> ORGANISM: Artificial
<220> FEATURE:
<223> OTHER INFORMATION: target clade 1

<400> SEQUENCE: 9
gtggcgaatg gggcatttgc agg                                              23

<210> SEQ ID NO 10
<211> LENGTH: 22
<212> TYPE: DNA
<213> ORGANISM: Artificial
<220> FEATURE:
<223> OTHER INFORMATION: target clade 1

<400> SEQUENCE: 10
ctcggagtag ctgcgtgagc tc                                               22

<210> SEQ ID NO 11
<211> LENGTH: 22
<212> TYPE: DNA
<213> ORGANISM: Artificial
<220> FEATURE:
<223> OTHER INFORMATION: target clade 1

<400> SEQUENCE: 11
gagctcggtc ttgaggccag cc                                               22

<210> SEQ ID NO 12
<211> LENGTH: 23
<212> TYPE: DNA
<213> ORGANISM: Artificial
<220> FEATURE:
<223> OTHER INFORMATION: target clade 1
```

<400> SEQUENCE: 12
tctggtaccc ggatcggggk agt                                           23

<210> SEQ ID NO 13
<211> LENGTH: 19
<212> TYPE: DNA
<213> ORGANISM: Artificial
<220> FEATURE:
<223> OTHER INFORMATION: target clade 1

<400> SEQUENCE: 13
ctctgggtga attgtgcaa                                                19

<210> SEQ ID NO 14
<211> LENGTH: 24
<212> TYPE: DNA
<213> ORGANISM: Artificial
<220> FEATURE:
<223> OTHER INFORMATION: target clade 1

<400> SEQUENCE: 14
gctctcagtt gtgcgttctc ggtg                                          24

<210> SEQ ID NO 15
<211> LENGTH: 22
<212> TYPE: DNA
<213> ORGANISM: Artificial
<220> FEATURE:
<223> OTHER INFORMATION: target clade 1

<400> SEQUENCE: 15
gaaggcttct tacggagctg at                                            22

<210> SEQ ID NO 16
<211> LENGTH: 20
<212> TYPE: DNA
<213> ORGANISM: Artificial
<220> FEATURE:
<223> OTHER INFORMATION: target clade 2

<400> SEQUENCE: 16
ggggytggtt gtccttctgt                                               20

<210> SEQ ID NO 17
<211> LENGTH: 34
<212> TYPE: DNA
<213> ORGANISM: Artificial
<220> FEATURE:
<223> OTHER INFORMATION: target clade 2

<400> SEQUENCE: 17
acccgggtcg ggggagtgct gtttgctctg ggtg                               34

<210> SEQ ID NO 18
<211> LENGTH: 45
<212> TYPE: DNA
<213> ORGANISM: Artificial
<220> FEATURE:
<223> OTHER INFORMATION: target clade 3

<400> SEQUENCE: 18
gggaagagtc cagcgctgaa tcgcatctcc yctggggatg tgagg                   45

<210> SEQ ID NO 19
<211> LENGTH: 22

-continued

<212> TYPE: DNA
<213> ORGANISM: Artificial
<220> FEATURE:
<223> OTHER INFORMATION: target clade 3

<400> SEQUENCE: 19
gaccgtaagc ttgggttggc cc 22

<210> SEQ ID NO 20
<211> LENGTH: 29
<212> TYPE: DNA
<213> ORGANISM: Artificial
<220> FEATURE:
<223> OTHER INFORMATION: target clade 3

<400> SEQUENCE: 20
aactagyggt gcctactcat ctttgcgtg 29

<210> SEQ ID NO 21
<211> LENGTH: 32
<212> TYPE: DNA
<213> ORGANISM: Artificial
<220> FEATURE:
<223> OTHER INFORMATION: target clade 3

<400> SEQUENCE: 21
acccgtctgt tgttggacgt tgggcttcct gc 32

<210> SEQ ID NO 22
<211> LENGTH: 22
<212> TYPE: DNA
<213> ORGANISM: Artificial
<220> FEATURE:
<223> OTHER INFORMATION: target clade 3

<400> SEQUENCE: 22
ggggtcggtt gtctttctgt tc 22

<210> SEQ ID NO 23
<211> LENGTH: 40
<212> TYPE: DNA
<213> ORGANISM: Artificial
<220> FEATURE:
<223> OTHER INFORMATION: target clade 3

<400> SEQUENCE: 23
ctgagatgct cggggtagct gcgtgaactc ggctttgagg 40

<210> SEQ ID NO 24
<211> LENGTH: 50
<212> TYPE: DNA
<213> ORGANISM: Artificial
<220> FEATURE:
<223> OTHER INFORMATION: target clade 3

<400> SEQUENCE: 24
acccgggtcg gggaatgct gtttactctg ggtgagagtg tgcaatggtt 50

<210> SEQ ID NO 25
<211> LENGTH: 23
<212> TYPE: DNA
<213> ORGANISM: Artificial
<220> FEATURE:
<223> OTHER INFORMATION: target clade 3

<400> SEQUENCE: 25

```
acacgtacca gcaatcagtt cgg                                                23

<210> SEQ ID NO 26
<211> LENGTH: 24
<212> TYPE: DNA
<213> ORGANISM: Artificial
<220> FEATURE:
<223> OTHER INFORMATION: target clade 3

<400> SEQUENCE: 26
aaaagccggt tatctgtccg accc                                               24

<210> SEQ ID NO 27
<211> LENGTH: 21
<212> TYPE: DNA
<213> ORGANISM: Artificial
<220> FEATURE:
<223> OTHER INFORMATION: target clade 4

<400> SEQUENCE: 27
aaacggacag agccggcgta t                                                  21

<210> SEQ ID NO 28
<211> LENGTH: 75
<212> TYPE: DNA
<213> ORGANISM: Artificial
<220> FEATURE:
<223> OTHER INFORMATION: target clade 4

<400> SEQUENCE: 28
ttgttgggca tgggctgyc agcttccaga ctggggcggy ggttcattwg tcytgyggct         60
catggggcat ttgca                                                         75

<210> SEQ ID NO 29
<211> LENGTH: 28
<212> TYPE: DNA
<213> ORGANISM: Artificial
<220> FEATURE:
<223> OTHER INFORMATION: target clade 4

<400> SEQUENCE: 29
gggtgtatgt gtgtgatggt cacgggtt                                           28

<210> SEQ ID NO 30
<211> LENGTH: 44
<212> TYPE: DNA
<213> ORGANISM: Artificial
<220> FEATURE:
<223> OTHER INFORMATION: target clade 4

<400> SEQUENCE: 30
acgtaccagc agttagttcg gtccggttcg ggctctcatt gcat                         44

<210> SEQ ID NO 31
<211> LENGTH: 23
<212> TYPE: DNA
<213> ORGANISM: Artificial
<220> FEATURE:
<223> OTHER INFORMATION: target clade 4

<400> SEQUENCE: 31
ggttatctgt ttgacccgtc ttg                                                23

<210> SEQ ID NO 32
<211> LENGTH: 68
```

```
<212> TYPE: DNA
<213> ORGANISM: Artificial
<220> FEATURE:
<223> OTHER INFORMATION: target clade 4

<400> SEQUENCE: 32
aaagtaaagg tgtccttgcg gaactgatgt gtgatcccga gcacttcggt gygagggcgc    60
aacatagt                                                            68

<210> SEQ ID NO 33
<211> LENGTH: 17
<212> TYPE: DNA
<213> ORGANISM: Artificial
<220> FEATURE:
<223> OTHER INFORMATION: target clade 5

<400> SEQUENCE: 33
tgagcttgga ytggccy                                                  17

<210> SEQ ID NO 34
<211> LENGTH: 20
<212> TYPE: DNA
<213> ORGANISM: Artificial
<220> FEATURE:
<223> OTHER INFORMATION: target clade 5

<400> SEQUENCE: 34
acccgggctg tgggagtgct                                               20

<210> SEQ ID NO 35
<211> LENGTH: 21
<212> TYPE: DNA
<213> ORGANISM: Artificial
<220> FEATURE:
<223> OTHER INFORMATION: target clade 6

<400> SEQUENCE: 35
cccttgatcg gggctccaga g                                             21

<210> SEQ ID NO 36
<211> LENGTH: 22
<212> TYPE: DNA
<213> ORGANISM: Artificial
<220> FEATURE:
<223> OTHER INFORMATION: target clade 6

<400> SEQUENCE: 36
tgtgctyttg ggcgtttgga tt                                            22

<210> SEQ ID NO 37
<211> LENGTH: 22
<212> TYPE: DNA
<213> ORGANISM: Artificial
<220> FEATURE:
<223> OTHER INFORMATION: target clade 6

<400> SEQUENCE: 37
tctgggtgct gagtggtgtg ca                                            22

<210> SEQ ID NO 38
<211> LENGTH: 19
<212> TYPE: DNA
<213> ORGANISM: Artificial
<220> FEATURE:
<223> OTHER INFORMATION: target clade 6
```

<400> SEQUENCE: 38
gatcccgtgc accacggtg 19

<210> SEQ ID NO 39
<211> LENGTH: 37
<212> TYPE: DNA
<213> ORGANISM: Artificial
<220> FEATURE:
<223> OTHER INFORMATION: clade 1 snp

<400> SEQUENCE: 39
ccaactggcg gtgcctaccc atctttacgt gtcttgg 37

<210> SEQ ID NO 40
<211> LENGTH: 27
<212> TYPE: DNA
<213> ORGANISM: Artificial
<220> FEATURE:
<223> OTHER INFORMATION: clade 1 snp

<400> SEQUENCE: 40
agactggggt ttgctgtcct tctgttc 27

<210> SEQ ID NO 41
<211> LENGTH: 28
<212> TYPE: DNA
<213> ORGANISM: Artificial
<220> FEATURE:
<223> OTHER INFORMATION: clade 1 snp

<400> SEQUENCE: 41
tcgggtccgt gttgactcga gctggggg 28

<210> SEQ ID NO 42
<211> LENGTH: 23
<212> TYPE: DNA
<213> ORGANISM: Artificial
<220> FEATURE:
<223> OTHER INFORMATION: clade 1 snp

<400> SEQUENCE: 42
cccaaaggcg caatgaaagt gaa 23

<210> SEQ ID NO 43
<211> LENGTH: 37
<212> TYPE: DNA
<213> ORGANISM: Artificial
<220> FEATURE:
<223> OTHER INFORMATION: clade 1 snp

<400> SEQUENCE: 43
ccaactggcg gcgcctaccc atctttacgt gtcttgg 37

<210> SEQ ID NO 44
<211> LENGTH: 47
<212> TYPE: DNA
<213> ORGANISM: Artificial
<220> FEATURE:
<223> OTHER INFORMATION: clade 2 snp

<400> SEQUENCE: 44
ctggcgtatc tggcttgcat tcacccgttt gttgttgcgc gttgggc 47

<210> SEQ ID NO 45
<211> LENGTH: 57

<210> SEQ ID NO 45
<211> LENGTH: 57
<212> TYPE: DNA
<213> ORGANISM: Artificial
<220> FEATURE:
<223> OTHER INFORMATION: clade 2 snp

<400> SEQUENCE: 45
ctggttgtcc ttctgtgcgg cggctgatgg ggcatttgca ggcggagtgc gccgaga      57

<210> SEQ ID NO 46
<211> LENGTH: 23
<212> TYPE: DNA
<213> ORGANISM: Artificial
<220> FEATURE:
<223> OTHER INFORMATION: clade 2 snp

<400> SEQUENCE: 46
tctgggtgca cagcgcggtg gtt      23

<210> SEQ ID NO 47
<211> LENGTH: 27
<212> TYPE: DNA
<213> ORGANISM: Artificial
<220> FEATURE:
<223> OTHER INFORMATION: clade 3 snp

<400> SEQUENCE: 47
agactggggt cggttgtctt tctgttc      27

<210> SEQ ID NO 48
<211> LENGTH: 18
<212> TYPE: DNA
<213> ORGANISM: Artificial
<220> FEATURE:
<223> OTHER INFORMATION: clade 3 snp

<400> SEQUENCE: 48
agcggctgat ggggcatt      18

<210> SEQ ID NO 49
<211> LENGTH: 21
<212> TYPE: DNA
<213> ORGANISM: Artificial
<220> FEATURE:
<223> OTHER INFORMATION: clade 3 snp

<400> SEQUENCE: 49
tgcaggcgga gtgcgctgag a 21

<210> SEQ ID NO 50
<211> LENGTH: 33
<212> TYPE: DNA
<213> ORGANISM: Artificial
<220> FEATURE:
<223> OTHER INFORMATION: clade 4 snp

<400> SEQUENCE: 50
agactggggc ggcggttcat twgtcytgyg gct 33

<210> SEQ ID NO 51
<211> LENGTH: 24
<212> TYPE: DNA
<213> ORGANISM: Artificial
<220> FEATURE:
<223> OTHER INFORMATION: clade 4 snp

<400> SEQUENCE: 51

```
ccttcggact ggtacccggg ctgg                                          24

<210> SEQ ID NO 52
<211> LENGTH: 33
<212> TYPE: DNA
<213> ORGANISM: Artificial
<220> FEATURE:
<223> OTHER INFORMATION: clade 4 snp

<400> SEQUENCE: 52
tggtcacggg ttcgtgcttg gtcgagctgg cgg                                33

<210> SEQ ID NO 53
<211> LENGTH: 40
<212> TYPE: DNA
<213> ORGANISM: Artificial
<220> FEATURE:
<223> OTHER INFORMATION: clade 5 snp

<400> SEQUENCE: 53
ctccagagaa ggtrcaagac ctgtccaacg ggtggttgcc                         40

<210> SEQ ID NO 54
<211> LENGTH: 25
<212> TYPE: DNA
<213> ORGANISM: Artificial
<220> FEATURE:
<223> OTHER INFORMATION: clade 5 snp

<400> SEQUENCE: 54
tggtgttcmt tctgctcagg gggct                                         25

<210> SEQ ID NO 55
<211> LENGTH: 29
<212> TYPE: DNA
<213> ORGANISM: Artificial
<220> FEATURE:
<223> OTHER INFORMATION: clade 5 snp

<400> SEQUENCE: 55
tgctcgggac agctgcatga gcttggctt                                     29

<210> SEQ ID NO 56
<211> LENGTH: 24
<212> TYPE: DNA
<213> ORGANISM: Artificial
<220> FEATURE:
<223> OTHER INFORMATION: clade 5 snp

<400> SEQUENCE: 56
ttgagctggt ggttggtggc ggtc                                          24

<210> SEQ ID NO 57
<211> LENGTH: 26
<212> TYPE: DNA
<213> ORGANISM: Artificial
<220> FEATURE:
<223> OTHER INFORMATION: clade 5 snp

<400> SEQUENCE: 57
gcgtgcgaca cgtgccggcr gtcagt                                        26

<210> SEQ ID NO 58
<211> LENGTH: 37
<212> TYPE: DNA
<213> ORGANISM: Artificial
```

```
<220> FEATURE:
<223> OTHER INFORMATION: clade 5 snp

<400> SEQUENCE: 58
atccgtgtgt tcttggacgt ttggattgcc actctcc                              37

<210> SEQ ID NO 59
<211> LENGTH: 35
<212> TYPE: DNA
<213> ORGANISM: Artificial
<220> FEATURE:
<223> OTHER INFORMATION: clade 5 snp

<400> SEQUENCE: 59
gcactccggt gtgcgggcgc aacatagtcc cgtcc                                35

<210> SEQ ID NO 60
<211> LENGTH: 28
<212> TYPE: DNA
<213> ORGANISM: Artificial
<220> FEATURE:
<223> OTHER INFORMATION: clade 5 snp

<400> SEQUENCE: 60
attggcctgc ttgttcaagt ttcccttg                                        28

<210> SEQ ID NO 61
<211> LENGTH: 20
<212> TYPE: DNA
<213> ORGANISM: Artificial
<220> FEATURE:
<223> OTHER INFORMATION: Gp forward primer

<400> SEQUENCE: 61
tgggatggtg ttcattctgc                                                 20

<210> SEQ ID NO 62
<211> LENGTH: 18
<212> TYPE: DNA
<213> ORGANISM: Artificial
<220> FEATURE:
<223> OTHER INFORMATION: Gp-reverse primer

<400> SEQUENCE: 62
caagctcatg cagctgtc                                                   18

<210> SEQ ID NO 63
<211> LENGTH: 18
<212> TYPE: DNA
<213> ORGANISM: Artificial
<220> FEATURE:
<223> OTHER INFORMATION: Gr-forward primer

<400> SEQUENCE: 63
gtgagcttgg attggcct                                                   18

<210> SEQ ID NO 64
<211> LENGTH: 18
<212> TYPE: DNA
<213> ORGANISM: Artificial
<220> FEATURE:
<223> OTHER INFORMATION: Gr-reverse primer

<400> SEQUENCE: 64
caagctcatg cagctgct                                                   18
```

METHOD FOR DETECTING CYST NEMATODES

RELATED APPLICATIONS

This application is a 35 U.S.C. §371 national phase application of PCT/NL2007/050700 (WO 2008/079012), filed on Dec. 21, 2007, entitled "Method for Detecting Cyst Nematodes", which application claims the benefit of European Application No. 06077326.4, filed Dec. 27, 2006, each of which is incorporated herein by reference in its entirety.

The present invention relates to a method for detecting plant pathogens. In particular it relates to a method for detecting nematodes that are pathogenic to plants, more in particular agricultural crop plants.

Nematodes (roundworms) are non-segmented invertebrate animals that constitute (or cover) an entire phylum (Phylum Nematoda). Most plant-parasitic nematodes cause root galls, rots and lesions and can severely retard root growth by feeding on plant roots. Some of these have a specially adapted mouth part—an odontostylet (a modified and enlarged tooth) or a stomatostylet (elongation of the stoma (Gr. mouth))—, allowing them to feed on plants. Nematodes produce eggs, and larvae undergo several moults before becoming plant-pathogenic adults. Nematodes are also troublesome because they can act as very efficient vectors of plant viruses. Plant parasitic nematodes are ubiquitous soil-borne pests that cause significant damage to most, if not all, crops growing in the tropics and subtropics. In cases where they interact simultaneously with root-rot or wilt pathogens they can cause enormous yield loss. Although actual losses on a per country basis are not known, estimates of annual losses exceeding 100 billion US dollars worldwide have been made (Luc et al., 1990). Particularly horticultural crops are heavily damaged by plant parasitic nematodes. In many cases, these losses are circumvented for short periods of time by yearly applications of expensive and highly toxic pre-plant application of fumigants (general biocides) or by the use of acetyl cholinesterase inhibitors (general insecticides/nematicides). These pesticides reduce early root penetration, but do not eradicate the nematode from the soil.

A particular group of plant pathogenic nematodes is formed by the cyst nematodes. In contrast to root-knot nematodes, whose eggs are maintained in a gelatinous matrix outside the female body and which do generally not survive winter conditions, cyst nematode eggs are maintained within the body of the female. After the death of the cyst female, the body becomes hard or tanned (the cyst) and protects the eggs from adverse environmental conditions. Eggs in cysts can remain viable for several years. While the poor survival of root-knot nematodes is compensated by a very wide host range that enables overwintering juveniles and those hatching from eggs in spring to reproduce on a variety of crop or weed hosts, the cyst nematodes have a more limited host range, often confined to a few plant species.

It is important to note that the economic aspects of plant pathogenicity are, at least in part, a direct result of developments in agricultural practice. Soybean, potato, (sugar)beet, and corn are just a few examples of plant species that are exotic to the agricultural production areas where cyst nematodes have become a pest. Due to the import of both host-plant and cyst nematode in the absence of natural predators or diseases, the natural ecologic balance is lost, and the cyst nematode became a pest. Wheat as a plant species is also "exotic" to many agricultural areas in the world, but is a major agricultural staple crop for thousands of years. As a result, a natural balance is restored in most growing areas. Although rice cyst nematodes exist, in tropical areas the effect of cyst nematodes is overshadowed by root knot nematodes. In general, adverse agricultural effects of nematodes on crops in the tropics are caused by root knot nematodes, while in temperate climatic zones cyst nematodes are a major concern.

The importance of the detection of nematodes, and in particular the correct identification of the nematodes in agricultural production soils, is exemplified by the fact that certain crops cannot be cultivated when the soils are infested with certain types of nematodes. For instance soils that are infested with potato cyst nematodes (PCN) can only be used for growing non-host crops or for growing PCN-resistant potato varieties. In fact, in many countries, testing of fields for PCN is mandatory under governmental regulations before any seed potato may be planted.

The problem with detection and identification is that morphological methods are too cumbersome and error-prone. The difference between the two major PCNs *Globodera rostochiensis* and *G. pallida* is, for instance, confined to a minor morphological difference in the knobs at the base of the stylet and the stylet length. Therefore, molecular methods have been proposed to distinguish between these two species. For instance, Pylypenko et al. (*Eur J Plant Pathol* (2005) 111:39-46) use the ITS (internal transcribed spacer 1 and 2—two non-coding rDNA fragments) sequences of ribosomal DNA to distinguish between *Globodera rostochiensis* and *G. pallida* by PCR. The problem with such a test is that it is based on a non-coding—hence moderate to highly variable—DNA region. Validation of such a test would require a world-wide survey to define the (substantial) within species variation. Moreover, the non-coding nature of these regions makes it is prone to change in time at a magnitude far higher than any of the coding ribosomal DNA regions. This may either result in false-negative or false-positive test results when the test is performed on soil samples in which the PCN population is uncharacterized. For instance, a test developed for potato cyst nematodes in the United Kingdom will not necessarily be suitable for detecting PCN in The Netherlands or Germany, because these populations are the result of another introduction from its centre of diversity—the Andean regions in South America.

Therefore, tests that are developed for the detection of cyst nematodes are of limited regional importance, and the detection methodology implies that it can be used at best for a few years (until the moment that—in the absence of any selection pressure—a random mutation undermines the test). It would however be economically advantageous to provide a test that performs consistently and that provides valuable results in a wide variety of growing areas with equal confidence.

Thus, one problem that the present invention aims to overcome, is the provision of a test for detection of nematodes which can be used on samples having uncharacterized populations of nematodes. Another problem that the present invention aims to overcome, is the provision of a test which provides important information on nematode presence in agricultural production soils in a wide range of agricultural regions of the world. Another problem that the present invention aims to overcome, is the provision of a test that is inherently stable over time (within a time frame of a few hundred years).

It has now surprisingly been found that these problem may be overcome by a method of the present invention.

In a first aspect, the present invention provides a method for determining the presence of a cyst nematode in a sample comprising the steps of:

providing a pair of bidirectional oligonucleotide primers or an oligonucleotide probe that hybridizes specifically, under stringent hybridization conditions, to a nucleic acid sequence encoding a Small Subunit (SSU) or Large Subunit (LSU) ribosomal RNA (rRNA) molecule, or the complement or transcript thereof, of a subgenus-cluster of nematodes, said subgenus-cluster comprising cyst nematodes belonging to at least one species of nematodes, and wherein said primers or oligonucleotide probe do not hybridize to a nucleic acid sequence encoding a Small Subunit (SSU) or Large Subunit (LSU) ribosomal RNA (rRNA) molecule of cyst nematodes that do not belong to (are not a part of) said subgenus cluster of cyst nematodes;

providing a sample in which the presence of the cyst nematode is to be detected, and performing a nucleic acid detection assay on said sample using said pair of bidirectional oligonucleotide primers or said oligonucleotide probe.

In another preferred embodiment, said cyst nematode is a nematode belonging to the family Heteroderidae, preferably to subfamilies Heteroderinae or Punctoderinae.

In yet another preferred embodiment, said sample is a soil sample, a root or tuber sample, a sample of soil attached to roots, a sediment or water bottom sample or a sludge sample.

In yet another preferred embodiment, said sample is a sample of cysts of cyst nematodes extracted (isolated) from a soil, root or tuber, sediment or sludge sample.

In yet another preferred embodiment, said sample of cysts, such as for instance extracted from soil, represents a mixed population comprising cysts of multiple species of nematodes.

In yet another preferred embodiment, said subgenus-cluster comprises cyst nematodes belonging to at least one species selected from the group consisting of *Heterodera schachtii, Heterodera glycines, Heterodera trifolii, Heterodera betae, Heterodera zeae, Heterodera litoralis, Heterodera avenae, Heterodera aucklandia, Heterodera mani, Heterodera goettingiana, Heterodera urticae, Globodera pallida, Globodera rostochiensis, Globodera tabacum, Globodera achilleae, Globodera millefolii, Globodera artemisiae*.

In a preferred embodiment said subgenus-cluster comprises cyst nematodes belonging to at least two species of nematodes.

In yet another preferred embodiment, in particular wherein said subgenus cluster comprises two or more species of nematodes, and when said nucleic acid to which the primers and probe hybridize under stringent conditions encodes the Large Subunit (LSU) ribosomal RNA (rRNA), the subgenus-cluster is selected from the following clusters:

1) the subgenus cluster consisting of the species *Heterodera schachtii, Heterodera glycines, Heterodera trifolii* and *Heterodera betae;*
2) the subgenus cluster consisting of the species *Heterodera zeae* and *Heterodera litoralis;*
3) the subgenus cluster consisting of the species *Heterodera avenae, Heterodera aucklandia* and *Heterodera mani;*
4) the subgenus cluster consisting of the species *Heterodera goettingiana* and *Heterodera urticae;*
5) the subgenus cluster consisting of the species *Globodera pallida, Globodera rostochiensis* and *Globodera tabacum;* and
6) the subgenus cluster consisting of the species *Globodera achilleae, Globodera millefolii* and *Globodera artemisiae.*

In yet another preferred embodiment, said detection assay comprises isolating nucleic acids from said sample or from said cysts and performing a nucleic acid amplification reaction on said isolated nucleic acids using said pair of bidirectional primers.

In another aspect, the present invention provides a pair of bidirectional oligonucleotide primers or an oligonucleotide probe that hybridizes specifically, under stringent hybridization conditions, to a nucleic acid sequence encoding a Small Subunit (SSU) or Large Subunit (LSU) ribosomal RNA (rRNA), or the complement or transcript thereof, of a subgenus-cluster of nematodes, said subgenus-cluster comprising cyst nematodes belonging to at least one species of nematode, and wherein said primers or probe do not hybridize to a nucleic acid sequence encoding a Small Subunit (SSU) or Large Subunit (LSU) ribosomal RNA (rRNA) or the complement or transcript thereof of cyst nematodes not part of said subgenus-cluster of cyst nematodes. In preferred embodiments of said primers and probes, said subgenus-cluster comprises at least two species of nematodes and said nucleic acid sequence encodes a Large Subunit (LSU) ribosomal RNA (rRNA).

In another aspect, the present invention provides a kit for use in detecting a nematode in a sample, said kit comprising: at least one pair of bidirectional oligonucleotide primers or at least one oligonucleotide probe as defined above; and at least one reagent for performing a nucleic acid amplification or hybridization reaction.

In another aspect, the present invention provides a method for determining the presence of a cyst nematode in a sample comprising the steps of:

providing a first pair of bidirectional oligonucleotide primers or an oligonucleotide probe that hybridizes specifically, under stringent hybridization conditions, to a nucleic acid sequence specifically encoding the LSU rRNA molecule, of a subgenus-cluster of nematodes, said subgenus-cluster comprising cyst nematodes belonging to at least two species of nematodes, and wherein said primers or oligonucleotide probe do not hybridize to a nucleic acid sequence specifically encoding the LSU rRNA molecule, or the complement or transcript thereof, of cyst nematodes that do not belong to said subgenus-cluster of cyst nematodes;

providing a sample in which the presence of the cyst nematode is to be detected;

performing a first nucleic acid detection assay on said sample using said first (subcluster-specific) pair of bidirectional oligonucleotide primers or said oligonucleotide probe;

providing a second pair of bidirectional oligonucleotide primers or an oligonucleotide probe that hybridizes specifically, under stringent hybridization conditions, to a nucleic acid sequence encoding a Small Subunit (SSU) or Large Subunit (LSU) ribosomal RNA (rRNA) molecule, or the complement or transcript thereof, of a subgenus-cluster of nematodes, said subgenus-cluster comprising cyst nematodes belonging to a single species of nematodes, and wherein said primers or oligonucleotide probe do not hybridize to a nucleic acid sequence encoding a Small Subunit (SSU) or Large Subunit (LSU) ribosomal RNA (rRNA)molecule of cyst nematodes that do not belong to said subgenus-cluster of cyst nematodes;

performing a second nucleic acid detection assay on said same sample using said second pair of (species specific) bidirectional oligonucleotide primers or said oligonucleotide probe.

Figure 11:
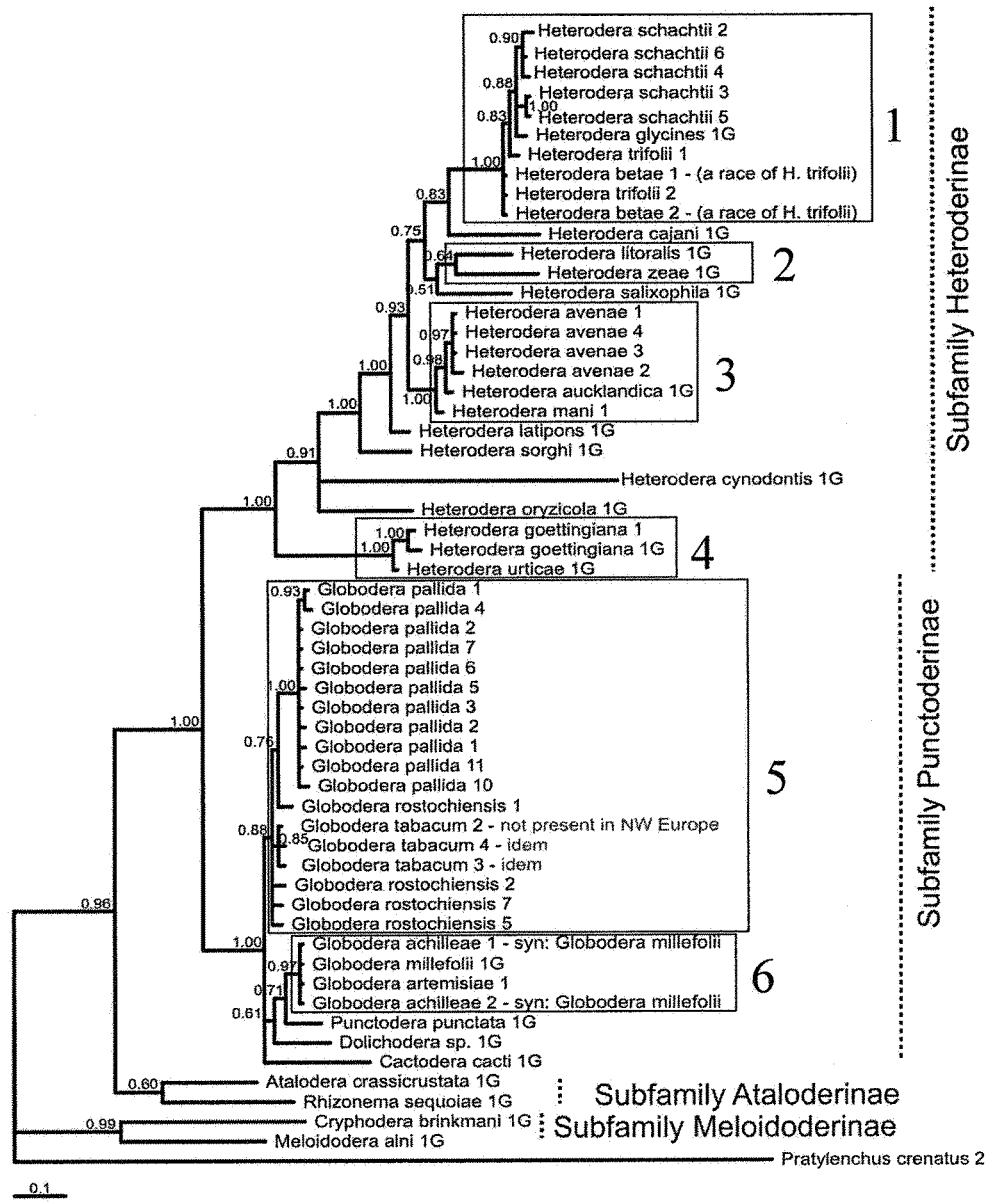

In a preferred embodiment, said second nucleic acid detection assay is performed dependent on the outcome of said first nucleic acid detection assay. The skilled person will appreciate that the two detection assays may be performed separately on the same sample. Preferably the first (subcluster-specific)

pair of bidirectional oligonucleotide primers or said oligonucleotide probe hybridize specifically, under stringent hybridization conditions, to a nucleic acid sequence specifically encoding the LSU rRNA molecule, or the complement or transcript thereof, of two or more species of nematodes as defined in clades 1-6 of FIG. 11. Preferably the second (species-specific) pair of bidirectional oligonucleotide primers or said oligonucleotide probe hybridize specifically, under stringent hybridization conditions, to a nucleic acid sequence encoding a Small Subunit (SSU) or Large Subunit (LSU) ribosomal RNA (rRNA)molecule, or the complement or transcript thereof, of a single nematode species. In this way a nested nucleic acid detection assay is provided wherein it is first determines on a broad scale whether cyst nematodes of a specific species of interest are (potentially) present in said sample, and wherein additionally it is determined in more detail which species of nematode is present in said sample.

The methods as described herein for detecting nematodes provide for assays for detecting cyst nematodes that have as an important advantage over previously available (ITS-based) assays that the assay is stable over time (or at least more stable than assays based on random mutations in highly variable (non-coding) genomic regions such as ITS regions), and that populations (samples) of various geographical origin can now be accurately and robustly assayed, since the sequences detected do not suffer from random mutations which are usually different from one population to another, because the sequences are coding regions.

In addition, it is a feature of certain embodiments of the present invention that subgenus clusters of nematodes are detected in a single nucleic acid detection format, based on a set of amplification primers or a single probe, wherein two or more species of nematode are detected, for instance the (sugar)beet cyst nematode *H. schachtii* as a first species and the soybean cyst nematode *H. glycines* as a second species. An importance advantage of this method is that a specific pair of bidirectional oligonucleotide primers may detect both the (sugar)beet cyst nematodes and soybean cyst nematodes alike, yet, the performance of such a test on a soil sample intended for growth of soybean will provide sufficient information for a specific agricultural purpose in a specific agricultural location.

As an example, the following situation is illustrative: the soybean cyst nematodes are not present in North Western Europe because the host plant is not present. Therefore, a negative result with a test performed with a pair of bidirectional oligonucleotide primers specific for (sugar)beet cyst nematodes and soybean cyst nematodes alike, provides the information that a (sugar)beet grower in North Western Europe requires for planting or seeding of (sugar)beets: the soil is free of the cyst nematodes that pose a threat to the intended crop, the (sugar)beet cyst nematode. In analogy, now that (sugar)beet cyst nematodes are of concern only to sugar beet growers, a negative test result with the same test will provide a soybean grower in Argentina with the information he/she requires for planting or seeding of soybean: the soil is free of the cyst nematodes that pose a threat to the intended crop, the soybean cyst nematode.

As another example, a positive test result with a pair of bidirectional oligonucleotide primers specific for *G. tabacum/G. pallidal/G. rostochiensis* is equally valuable in tobacco growing areas of the US such as Virginia, as it is in a potato growing area of the US such as Idaho: A positive test result in an intended tobacco field or in an intended potato field are interpreted entirely differently, yet provide the grower with valuable information.

Another advantage of the detection of subgenus-clusters is that combination of two such tests can confirm the presence of a pathogenic cluster while confirming the absence of a non-pathogenic cluster. This cannot be performed with any prior art methods, which would effectively require the performance of a large number of different species-specific tests, or would require the validation of a test to the level that all regional variations between strains of nematodes from a single species are covered. This is not practical. For instance, the potato pathogens *G. rostochiensis* en *G. pallida* cannot easily be distinguished from the species a *G. millefolii* (syn. *G. achilleae*) and/or *G. artemisiae*, which are not pathogenic to potato. By using the present method, it becomes possible to provide a test result with which the presence of the non-pathogenic species can positively be excluded. Moreover, now that the clustering of *G. rostochiensis* en *G. pallida* in a single test provides for a genetic variation wider than the species level, the possible variation in strain level is covered at least to a certain extent. It should be stressed that due to the sub-genus level of detection, any cross-reactivity with other species within the genus is a priory excluded, so that the second subgenus-cluster test is a mere confirmation.

Thus, the present inventors have now discovered that the specific host-range, the consequential link in geological distribution of nematodes and host plants, and the specific agricultural use of different soils in the world, makes the detection of nematodes in the form of sub-genus clusters extremely valuable, while at the same time providing for a very robust testing system.

The sub-genus level of detection as proposed herein provides for a more robust molecular detection system for the following reasons. It is a general mechanism in molecular evolution that nucleic acid sequences comprise conserved and variable regions. The rate of mutation between separated populations is particularly notable in the sequence differences in variable regions, while conserved regions have sequences that are in common between many species and even genera. For instance, when based on rRNA sequences of the large ribosomal subunit (LSU) of the nematode ribosome, stable phylogenetic divergence can be found among the various subgenera of the family Heteroderidae. In fact, the subfamilies Heteroderinae and Punctoderinae show stable divergence between sub-genus clusters.

Thus, the present inventors discovered by ribosomal sequence comparison that the major agricultural cyst nematodes could be covered by assigning only six agriculturally significant sub-genus clusters on the basis of their LSU rRNA sequence. An overview of the agricultural significance of the test system as proposed herein is provided in Table 2 in the Examples.

The skilled person will appreciate that due to the same principle of linkage between the geographic distribution of the host plants and cyst nematode, the intended agricultural use of a soil, and the possibility of detecting selected nematode species in the form of subgenus clusters, it is possible to device tests for sub-family level detection. Thus, as can be seen in FIG. 1, the assignment of a subfamily cluster Heteroderinae, and another subfamily cluster Punctoderinae, will allow the agriculturally significant detection of *Heterodera* species and *Globodera* species separately. However valuable such a test may be in some instances, a quick glance at an isolated cyst sample will be more rapid in discerning whether the cyst is lemon-shaped (*Heterodera*) or spherical (*Globodera*). The term subgenus-level is therefore not intended to be limited to a level below that of the genus per sé, although it is preferred.

As stated above, the nematode detected in a method of the invention is preferably a nematode belonging to the family Heteroderidae, more preferably to subfamilies Heteroderinae or Punctoderinae.

Although the sample used in a method of the invention may be any sample, such as a natural sample (e.g. a water-sample, a sample of a plant, or a soil sample), or a processed sample (e.g. a sample of isolated nucleic acids) the sample is preferably a soil sample. In highly preferred embodiments, the soil sample is a sample of nematode cysts extracted from soil.

Methods for extracting nematode cysts from soil are well known to the skilled artisan. The recovery of nematode cysts from soil differs essentially from the collection of alive, vermiform nematodes. Using the methods described below, nematodes cysts are isolated specifically, co-isolation of vermiform nematodes is highly unlikely. Various methods can be used to recover cysts from soil. In many cases air-dried soil is used because after addition of water cysts will float (together with organic debris). Depending on the nematode species, cyst can be caught by a sieve with 0.10 to 0.25 mm openings. A number of methods have been developed to permit large scale soil washing operations for the recovery of cysts. Below three methods will be shortly introduced (all three are used by commercial soil analysis laboratories):

1. Fenwick can method. The Fenwick can is used for the extraction of cysts from dried soil (max. 300 g). The method makes use of floating properties of dried cysts and of difference in size between and other fractions of the sample. In this method, coarse sample material is retained on the sieve, heavy particles passing through sink to the bottom of the can, and fine and light particles, like cysts, keep afloat. When the can overflows, the floating cysts are carried off over the overflow collar, and drop on a sieve with a pore size smaller than the cyst diameter.

2. Kort's cyst extraction elutriator. The Kort's cyst extraction elutriator (Kort elutriator) is used for extraction of cysts from soil (max 300 g). Drying the sample is not necessary. Therefore this method is recommended for the extraction of *Heterodera* and *Punctodera* (if a living cyst content is required). The method makes use of differences in sedimentation rate and size between cysts and soil particles. In the Kort elutriator, an undercurrent keeps the cysts afloat, while soil particles settle. The cysts are carried away with the overflowing water, and stay behind on a sieve with a pore size smaller than the cyst diameter.

3. Seinhorst cyst extraction elutriator. The Seinhorst cyst extraction apparatus (Seinhorst elutriator) is used for the extraction of cysts from soil (max 300 g). The sample does not need to be dried; therefore it is recommended for the extraction of *Heterodera* and *Punctodera* (if a living cyst content is required). The method makes use of differences in sedimentation rate and size between cysts and soil particles. In the Seinhorst funnel, an undercurrent keeps the cysts afloat while soil particles settle. The cysts are carried away with the overflowing water and stay behind on a sieve with smaller pore size than the cyst diameter. According to Seinhorst, (1964) mainly the light (half) empty cysts are washed onto the sieve, while heavy, full cysts keep afloat in the upper half of the funnel. For that reason the elutriator has a side-outlet to tap the content of the upper half of the funnel, which is also passed through the sieve.

4. Isolating cysts with organic solvents. The method is used for isolating cysts from debris left on the sieve after using one of the extraction methods for cysts described earlier. The debris needs to be well-dried. The method is especially reliable for *Globodera* spp. For many other cysts species, for example the pea cyst (*H. goettingiana*), the cysts are not sufficiently 'closed' (they have open 'windows', weak spots, and cracks); the extraction fluid rapidly enters the cyst, causing it to sink, so that it is lost for analysis. The method makes use of difference in structure between cysts and the debris retained after extraction with one of the methods described earlier. The dried debris is submerged in an organic solvent. Because of the low surface tension the 'closed' cysts keep afloat, while the porous organic debris absorbs the fluid and sinks. Commonly used extraction fluids are acetone ($CH_3COCH_3$), alcohol 96% ($C_2H_5OH$) and mixtures of acetone or ethanol with carbon tetrachloride ($CCl_4$).

When processing soil, it is possible that more than one species of cyst nematodes is present. Therefore, in a method for determining the presence of a nematode in a sample, the cysts extracted from soil suitably represents a mixed population comprising cysts of multiple species of nematodes.

A sample as defined herein may also comprise one or more isolated cysts, or even eggs, juveniles or adult nematodes.

In preferred embodiments of a method of the present invention the subgenus-cluster comprises at least two species selected from the group consisting of *Heterodera schachtii, Heterodera glycines, Heterodera trifolii, Heterodera betae, Heterodera zeae, Heterodera litoralis, Heterodera avenae, Heterodera aucklandia, Heterodera mani, Heterodera goettingiana, Heterodera urticae, Globodera pallida, Globodera rostochiensis, Globodera tabacum, Globodera achilleae* (equivalent to *Globodera millefolii*), *Globodera artemisiae*.

Preferably, the subgenus-cluster is selected from the following clusters:
1) the subgenus cluster consisting of the species *Heterodera schachtii, Heterodera glycines, Heterodera trifolii* and *Heterodera betae*;
2) the subgenus cluster consisting of the species *Heterodera zeae* and *Heterodera litoralis*;
3) the subgenus cluster consisting of the species *Heterodera avenae, Heterodera aucklandia* and *Heterodera mani*;
4) the subgenus cluster consisting of the species *Heterodera goettingiana* and *Heterodera urticae*;
5) the subgenus cluster consisting of the species *Globodera pallida, Globodera rostochiensis* and *Globodera tabacum*; and
6) the subgenus cluster consisting of the species *Globodera achilleae, Globodera millefolii* and *Globodera artemisiae*.

The primers or probes as used in a method of the invention are designed to hybridize a nucleic acid sequence encoding a Small Subunit (SSU) or Large Subunit (LSU) ribosomal RNA (rRNA) molecule of the cyst nematodes. When detecting multi-species subgenus clusters, the detection is preferably based on LSU rRNA sequences, which in nematodes, corresponds to the 28S rRNA. It was found that these sequences exhibit a level of evolutionary conservation very suitable for multi-species sub-genus level detection, that is, that they are not too conserved to prevent any distinction between species and clusters of species, yet conserved enough to allow for the development of a stable assay system suitable for application on samples from different geographical origin. The subgenus clusters comprising two or more species of nematodes are preferably as described in FIG. 11, more in particular consisting of the species as defined in clades 1 through 6 as indicated in FIG. 11.

The terms "hybridise" or "anneal" refer to the process by which single strands of nucleic acid sequences form double-helical segments through hydrogen bonding between complementary nucleotides.

The term "oligonucleotide" refers to a short sequence of nucleotide monomers (usually 6 to 100 nucleotides) joined by phosphorous linkages (e.g., phosphodiester, alkyl and arylphosphate, phosphorothioate), or non-phosphorous linkages (e.g., peptide, sulfamate and others). An oligonucleotide may contain modified nucleotides having modified bases (e.g., 5-methyl cytosine) and modified sugar groups (e.g., 2'-O-methyl ribosyl, 2'-O-methoxyethyl ribosyl, 2'-fluoro ribosyl, 2'-amino ribosyl, and the like). Oligonucleotides may be naturally-occurring or synthetic molecules of double- and single-stranded DNA and double- and single-stranded RNA with circular, branched or linear shapes and optionally including domains capable of forming stable secondary structures (e.g., stem-and-loop and loop-stem-loop structures).

The term "primer" as used herein refers to an oligonucleotide which is capable of annealing to the amplification target allowing a DNA polymerase to attach thereby serving as a point of initiation of DNA synthesis when placed under conditions in which synthesis of primer extension product which is complementary to a nucleic acid strand is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxy ribonucleotide. The primer must be sufficiently long to prime the synthesis of extension products in the presence of the agent for polymerization. The exact lengths of the primers will depend on many factors, including temperature and source of primer. A "pair of bi-directional primers" as used herein refers to one forward and one reverse primer as commonly used in the art of DNA amplification such as in PCR amplification, and may be directed to the coding strand of the DNA or the complementary strand.

The term "probe" refers to a single-stranded oligonucleotide sequence that will recognize and form a hydrogen-bonded duplex with a complementary sequence in a target nucleic acid sequence analyte or its cDNA derivative.

The terms "stringency" or "stringent hybridization conditions" refer to hybridization conditions that affect the stability of hybrids, e.g., temperature, salt concentration, pH, formamide concentration and the like. These conditions are empirically optimised to maximize specific binding and minimize non-specific binding of primer or probe to its target nucleic acid sequence. The terms as used include reference to conditions under which a probe or primer will hybridise to its target sequence, to a detectably greater degree than other sequences (e.g. at least 2-fold over background). Stringent conditions are sequence dependent and will be different in different circumstances. Longer sequences hybridise specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridises to a perfectly matched probe or primer. Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1 M NaCl, 1% SDS at 37° C., and a wash in 0.1×SSC at 60° C. Hybridization procedures are well known in the art and are described in e.g. Ausubel et al, Current Protocols in Molecular Biology, John Wiley & Sons Inc., 1994.

A "complement" or "complementary sequence" is a sequence of nucleotides which forms a hydrogen-bonded duplex with another sequence of nucleotides according to Watson-Crick base-paring rules. For example, the complementary base sequence for 5'-AAGGCT-3' is 3'-TTCCGA-5'.

Methods of the invention can in principle be performed by using any nucleic acid amplification method, such as the Polymerase Chain Reaction (PCR; Mullis 1987, U.S. Pat. Nos. 4,683,195, 4,683,202, en 4,800,159) or by using amplification reactions such as Ligase Chain Reaction (LCR; Barany 1991, Proc. Natl. Acad. Sci. USA 88:189-193; EP Appl. No., 320,308), Self-Sustained Sequence Replication (3SR; Guatelli et al., 1990, Proc. Natl. Acad. Sci. USA 87:1874-1878), Strand Displacement Amplification (SDA; U.S. Pat. Nos. 5,270,184, en 5,455,166), Transcriptional Amplification System (TAS; Kwoh et al., Proc. Natl. Acad. Sci. USA 86:1173-1177), Q-Beta Replicase (Lizardi et al., 1988, Bio/Technology 6:1197), Rolling Circle Amplification (RCA; U.S. Pat. No. 5,871,921), Nucleic Acid Sequence Based Amplification (NASBA), Cleavase Fragment Length Polymorphism (U.S. Pat. No. 5,719,028), Isothermal and Chimeric Primer-initiated Amplification of Nucleic Acid (ICAN), Ramification-extension Amplification Method (RAM; U.S. Pat. Nos. 5,719,028 and 5,942,391) or other suitable methods for amplification of DNA.

In order to amplify DNA with a small number of mismatches to one or more of the amplification primers, an amplification reaction may be performed under conditions of reduced stringency (e.g. a PCR amplification using an annealing temperature of 38° C., or the presence of 3.5 mM MgCl2). The person skilled in the art will be able to select conditions of suitable stringency.

Polynucleotides have "homologous" sequences if the sequence of nucleotides in the two sequences is the same when aligned for maximum correspondence as described herein. Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence homology" for polynucleotides, such as 50, 60, 70, 80, 90, 95, 98, 99 or 100 percent sequence homology may be determined by comparing two optimally aligned sequences over a comparison window, wherein the portion of the polynucleotide sequence in the comparison window may include additions or deletions (i.e. gaps) as compared to the reference sequence (which does not comprise additions or deletions) for optimal alignment of the two sequences. The percentage is calculated by: (a) determining the number of positions at which the identical nucleic acid base occurs in both sequences to yield the number of matched positions; (b) dividing the number of matched positions by the total number of positions in the window of comparison; and (c) multiplying the result by 100 to yield the percentage of sequence homology. Optimal alignment of sequences for comparison may be conducted by computerized implementations of known algorithms, or by inspection. Readily available sequence comparison and multiple sequence alignment algorithms are, respectively, the Basic Local Alignment Search Tool (BLAST) (Altschul, S. F. et al. 1990. J. Mol. Biol. 215:403; Altschul, S. F. et al. 1997. Nucleic Acid Res. 25:3389-3402) and ClustalW programs both available on the internet. Other suitable programs include GAP, BESTFIT and FASTA in the Wisconsin Genetics Software Package (Genetics Computer Group (GCG), Madison, Wis., USA).

As used herein, "substantially complementary" means that two nucleic acid sequences have at least about 65%, preferably about 70%, more preferably about 80%, even more preferably 90%, and most preferably about 98%, sequence complementarity to each other. This means that the primers and probes must exhibit sufficient complementarity to their template and target nucleic acid, respectively, to hybridise under stringent conditions. Therefore, the primer sequences as disclosed in this specification need not reflect the exact sequence of the binding region on the template and degenerate primers can be used. A substantially complementary primer sequence is one that has sufficient sequence complementarity to the amplification template to result in primer binding and second-strand synthesis. It is possible to use primer sequences containing e.g. inositol residues or ambiguous bases or even primers that contain one or more mismatches when compared to the target sequence. In general, sequences that exhibit at least 65%, more preferably at least 80% homology with the target DNA oligonucleotide sequences, are considered suitable for use in a method of the present invention. Sequence mismatches are also not critical when using low stringency hybridization conditions.

The term "hybrid" refers to a double-stranded nucleic acid molecule, or duplex, formed by hydrogen bonding between complementary nucleotides. The terms "hybridise" or "anneal" refer to the process by which single strands of nucleic acid sequences form double-helical segments through hydrogen bonding between complementary nucleotides.

The detection of the amplification products can in principle be accomplished by any suitable method known in the art. The detection fragments may be directly stained or labelled with radioactive labels, antibodies, luminescent dyes, fluorescent dyes, or enzyme reagents. Direct DNA stains include for example intercalating dyes such as acridine orange, ethidium bromide, ethidium monoazide or Hoechst dyes.

Alternatively, the DNA fragments may be detected by incorporation of labelled dNTP bases into the synthesized DNA fragments. Detection labels which may be associated with nucleotide bases include e.g. fluorescein, cyanine dye or BrdUrd.

When using a probe-based detection system, a suitable detection procedure for use in the present invention may for example comprise an enzyme immunoassay (EIA) format (Jacobs et al., 1997, J. Clin. Microbiol. 35, 791-795). For performing a detection by manner of the EIA procedure, either the forward or the reverse primer used in the amplification reaction may comprise a capturing group, such as a biotin group for immobilization of target DNA PCR amplicons on e.g. a streptavidin coated microtiter plate wells for subsequent EIA detection of target DNA amplicons (see below). The skilled person will understand that other groups for immobilization of target DNA PCR amplicons in an EIA format may be employed.

Probes useful for the detection of the target DNA as disclosed herein preferably bind only to at least a part of the DNA sequence region as amplified by the DNA amplification procedure. Those of skill in the art can prepare suitable probes for detection based on the nucleotide sequence of the target DNA without undue experimentation as set out herein. Also the complementary sequences of the target DNA may suitably be used as detection probes in a method of the invention, provided that such a complementary strand is amplified in the amplification reaction employed.

Suitable detection procedures for use herein may for example comprise immobilization of the amplicons and probing the DNA sequences thereof by e.g. southern blotting. Other formats may comprise an EIA format as described above. To facilitate the detection of binding, the specific amplicon detection probes may comprise a label moiety such as a fluorophore, a chromophore, an enzyme or a radio-label, so as to facilitate monitoring of binding of the probes to the reaction product of the amplification reaction. Such labels are well-known to those skilled in the art and include, for example, fluorescein isothiocyanate (FITC), b-galactosidase, horseradish peroxidase, streptavidin, biotin, digoxigenin, 35S or 125I. Other examples will be apparent to those skilled in the art.

Detection may also be performed by a so called reverse line blot (RLB) assay, such as for instance described by Van den Brule et al. (2002, J. Clin. Microbiol. 40, 779 787). For this purpose RLB probes are preferably synthesized with a 5'amino group for subsequent immobilization on e.g. carboxyl coated nylon membranes. The advantage of an RLB format is the ease of the system and its speed, thus allowing for high throughput sample processing.

The use of nucleic acid probes for the detection of DNA fragments is well known in the art. Mostly these procedure comprise the hybridization of the target DNA with the probe followed by post-hybridization washings. Specificity is typically the function of post-hybridization washes, the critical factors being the ionic strength and temperature of the final wash solution. For DNA-DNA hybrids, the Tm can be approximated from the equation of Meinkoth and Wahl, Anal. Biochem., 138: 267-284 (1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, The hybridization and/or wash conditions can be adjusted to hybridize to sequences of the desired identity. For example, if sequences with >90% identity are sought, the Tm can be decreased 10 C. Generally, stringent conditions are selected to be about 5 C lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier. New York (1993); and Current Protocols in Molecular Biology, Chapter 2, Ausubel, et al., Eds., Greene Publishing and Wiley-Interscience, New York (1995).

In another aspect, the invention provides oligonucleotide probes for the generic detection of target DNA. The detection probes herein are selected to be "substantially" complementary to one of the strands of the double stranded DNA amplicons generated by an amplification reaction of the invention. Preferably the probes are substantially complementary to the immobilizable, e.g. biotin labelled, antisense strands of the amplicons generated from the target DNA.

It is allowable for detection probes of the present invention to contain one or more mismatches to their target sequence. In general, sequences that exhibit at least 65%, more preferably at least 80% homology with the target DNA oligonucleotide sequences are considered suitable for use in a method of the present invention.

In a particularly preferred embodiment of the present invention, the method comprises a detection assay wherein nucleic acids from the sample are isolated and wherein a nucleic acid amplification reaction is performed by using a pair of bidirectional primers according to the present invention.

A pair of bidirectional oligonucleotide primers that hybridize specifically, under stringent hybridization conditions, to the nucleic acid (RNA or DNA) of a subgenus-cluster of nematodes as defined above is therefore also an aspect of the present invention, as is an oligonucleotide probe that hybridizes specifically, under stringent hybridization conditions, to the nucleic acid (RNA or DNA) of a subgenus-cluster of nematodes as defined above.

A further aspect of the present invention is a kit-of-parts for use in a method for detecting a nematode in a sample, said kit comprising at least one pair of bidirectional oligonucleotide primers as described herein above, or at least one oligonucleotide probe described herein above; and at least one reagent for performing a nucleic acid amplification or hybridization reaction.

The present inventors further discovered that based on LSU sequence data, single-species probes and primers may be developed that exhibit improved performance when compared to other sequence data, for instance SSU sequence data. For instance, the present inventors have discovered that a distinction between *G. pallida* and *G. rostochiensis* is possible based on sequence data of the LSU rRNA that provides for a better separation of signals derived from target versus those derived from non-target organisms. In fact, the present inventors discovered that while on SSU rRNA data, the ΔCt, or the difference in the cycle number in an Real-time PCR amplification reaction at which the fluorescent signal exceeds the threshold value between a target rostochiensis and a non-target pallida at equal concentration of template nucleic acids is around 20 cycles (see Holterman et al. Mol. Biol. Evol. (2006) 23:1792-1800). This means that when template nucleic acid concentrations are skew, i.e. when non-target template concentration exceeds by far the target template concentration, a false positive result is very likely. The present inventors have now found that based on LSU rRNA data, the ΔCt may be increased and the probability of false positive tests is reduced.

Therefore, in still another aspect, the present invention relates to a method for determining the presence of a nematode in a sample comprising the steps of:

providing a pair of bidirectional oligonucleotide primers or an oligonucleotide probe that hybridizes specifically, under stringent hybridization conditions, to the LSU rRNA or the corresponding DNA, sequence, or its complement, of a single nematode species;

providing a sample in which the presence of the nematode is to be detected, and performing a nucleic acid detection assay on said sample using said pair of bidirectional oligonucleotide primers or said oligonucleotide probe.

Preferably, such a method is performed to detect a nematode belonging to the family Heteroderidae, preferably to subfamilies Heteroderinae or Punctoderinae.

As stated for the method wherein sub-genus clusters of nematodes are detected, the method for detecting a single-species of nematode may be performed on any sample, preferably a soil sample. Suitably, the soil sample is a sample of cysts extracted from soil, for instance representing a mixed population comprising cysts of multiple species of nematodes.

In particularly preferred embodiments of the method for detecting a single-species of nematode, said nematode is selected from the group consisting of *Heterodera schachtii, Heterodera glycines, Heterodera trifolii, Heterodera betae, Heterodera zeae, Heterodera litoralis, Heterodera avenge, Heterodera aucklandia, Heterodera mani, Heterodera goettingiana, Heterodera urticae, Globodera pallida, Globodera rostochiensis, Globodera tabacum, Globodera achilleae* (equivalent to *Globodera millefolii*), and *Globodera artemisiae*.

Additional aspects of the present invention are a pair of bidirectional oligonucleotide primers or an oligonucleotide probe that hybridizes specifically, under stringent hybridization conditions, to the LSU rRNA or the corresponding DNA, sequence, or its complement, of a single nematode species as defined herein above.

Exemplary sequences that may be used as targets for such primers and probes are provided in SEQ ID NOs: 2-60.

In still another aspect, the present invention provides for a method for determining the presence of a nematode in a sample comprising the steps of performing in combination, a method of the invention wherein a sub-genus cluster is detected, and a method according to the present invention wherein a single species is detected. Such methods may be performed simultaneously or subsequently in any order. Preferably, a method wherein a sub-genus cluster is detected is performed first, so as to provide initial results which would require more detailed investigation by using species-specific detection method.

The invention will now be illustrated by means of the following, non-limiting examples.

LEGEND TO THE FIGURES

FIG. 1. Geographic distribution of *H. schachtii*
FIG. 2. Geographic distribution of *H. glycines*
FIG. 3. Geographic distribution of *H. trifolii*
FIG. 4. Geographic distribution of *H. zeae*
FIG. 5. Geographic distribution of *H. avenae*
FIG. 6. Geographic distribution of *H. goettingiana*
FIG. 7. Geographic distribution of *G. pallida*
FIG. 8. Geographic distribution of *G. tabacum*
FIG. 9. Geographic distribution of *G. rostochiensis*
FIG. 10. Geographic distribution of *H. oryzicola*
FIG. 11 LSU-rDNA based Heteroderidae tree indicating the 6 agriculturally important subgenus clusters of the present invention.
FIG. 12 provides a consensus sequence for the LSU-rDNA of the 6 agriculturally important subgenus clusters of the present invention. This consensus sequence provides the numbering for the SEQ ID NOs:1-60 of FIGS. 13-23.

FIGS. 13-23 provide exemplary target regions for a member of a pair of bidirectional oligonucleotide primers or for an oligonucleotide probe according to the present invention that hybridizes specifically, under stringent hybridization conditions, to the LSU rRNA or the corresponding DNA sequence or its complement, of a nematode of an agriculturally important subgenus cluster of the present invention or to a single nematode species as defined herein. The underlined nucleotide positions represent SNPs which, either alone, or in combination with an adjacent SNP or an SNP present in the same nucleic acid at a position no more than about 2 to 40, preferably 2 to 25, more preferably 2-10 contiguous nucleotides in the 3' or 5' direction of that SNP, provide species- or subgenus-cluster-specificity. The skilled person will understand that the probe or primer may also be targeted to the strand complementary to that indicated by the sequences presented, which are parts of the coding strand.

EXAMPLES

Example 1

Subgenus Clusters

The geographical distribution of *H. schachtii, H. glycines, H. trifolii, H. zeae, H. avenae, H. goettingiana, G. pallida, G. tabacum, G. rostochiensis* and *H. oryzicola* are provided in FIGS. 1-10. The information was obtained from CAB International. For the other nematodes listed in Table 1, the information was obtained from literature data and personal communications.

Based on LSU rDNA data a phylogenetic tree could be established which allowed the division of the entire family into only 5 agriculturally important clusters as described herein (see Table 2 and FIG. 11). The 6$^{th}$ cluster is a reference cluster. The testing scheme of Table 2 was based on the data provided in Table 1.

TABLE 1

Details of the subgenus-clusters of cyst nematodes proposed in the present invention.

Figure 2:
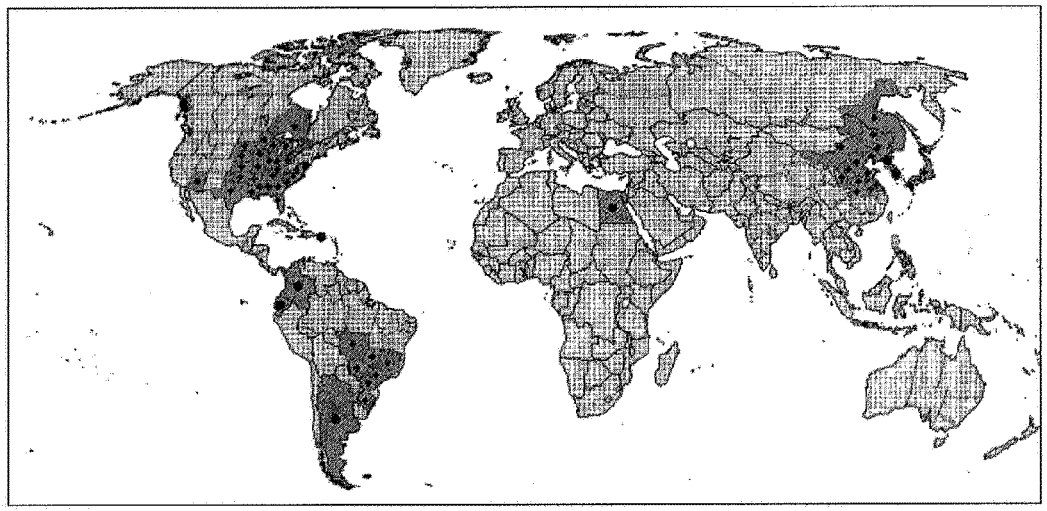
Figure 3:
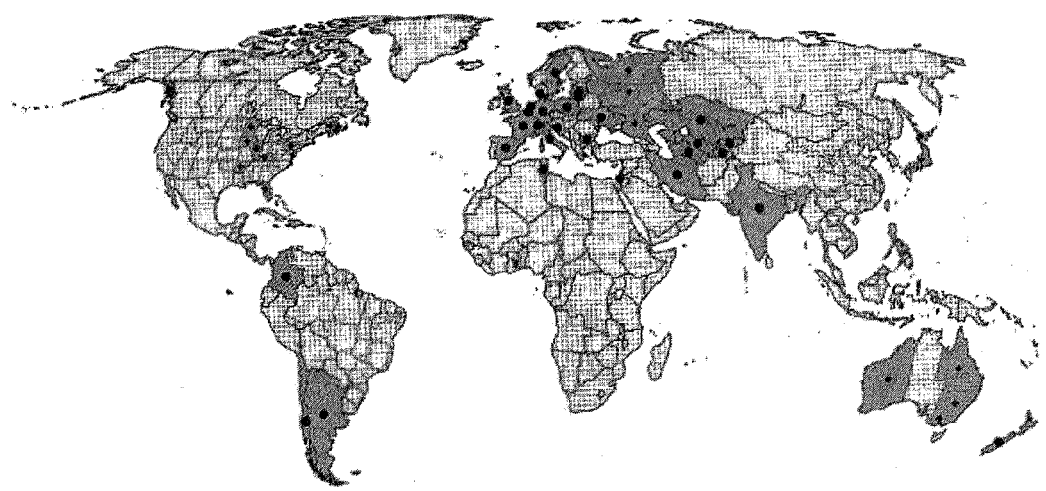
Figure 4:
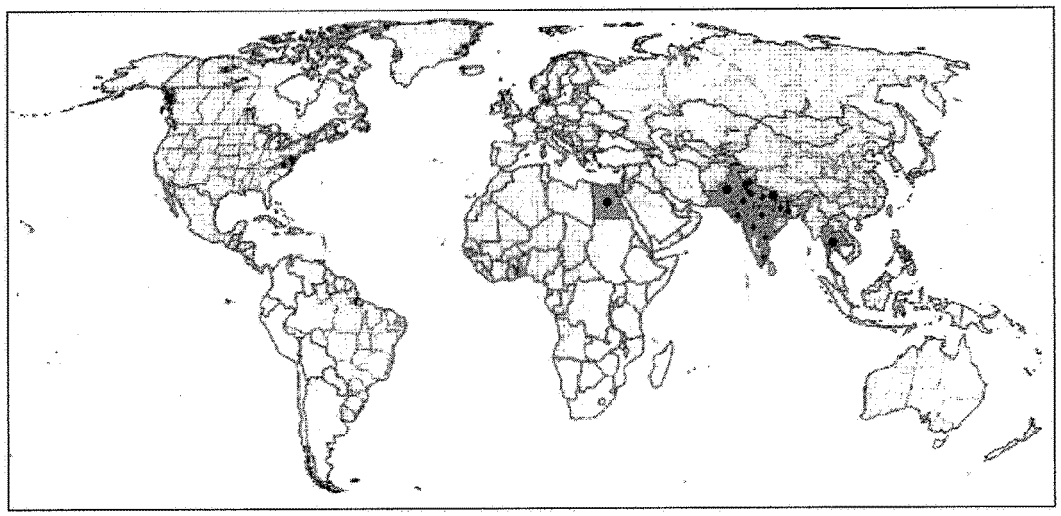
Figure 5:
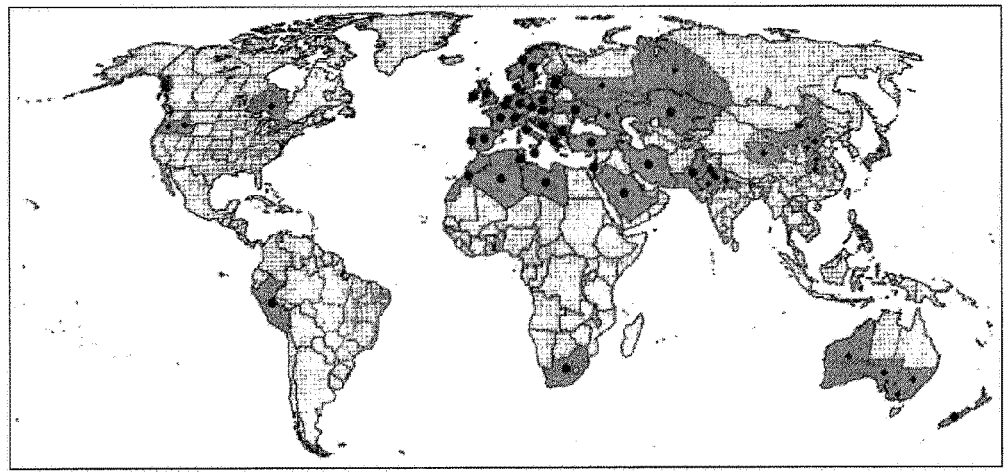

| Species | Subgenus Cluster (FIG. 11) | Distribution | Host crop | Non-crop host |
|---|---|---|---|---|
| *Heterodera schachtii* | 1 | see FIG. 1 | Sugarbeet (*Beta vulgaris*) and Brassicaceae | |
| *Heterodera glycines* | 1 | see FIG. 2 | Soybean (*Glycine max*) | |
| *Heterodera trifolii* | 1 | see FIG. 3 | A wide range of crops including cereals (Poaceae), Sugarbeet (*beta vulgaris*), and potato (*Solunum tuberosum*) | clover (*Trifolium* spp.) |
| *Heterodera betae* | 1 | no map available; presumably similar to *H. trifolii* | Sugarbeet (*Beta vulgaris*) | Cruciferae, Chenopodiaceae, Polygonaceae, some Leguminosae |
| *Heterodera zeae* | 2 | see FIG. 4 | Maize (*Zea mays*) | |
| *Heterodera litoralis* | 2 | New Zealand | — | Austral glasswort and possibly other Chenopodiaceae |
| *Heterodera avenae* | 3 | see FIG. 5 | Cereals (Poaceae), incl. barley, rye, wheat, oat | |
| *Heterodera aucklandia* | 3 | New Zealand | — | Rice grass (*Microlaena stipoides*) |
| *Heterodera mani* | 3 | Northern Ireland, various locations in Germany, various locations in France. Overall distribution presumably similar to *H. avenae* | Various Cereals (Poaceae) | |
| *Heterodera goettingiana* | 4 | see FIG. 6 | *Fabaceae*, mainly pea (*pisum sativum*) and broad bean (*Vicia faba*) | |
| *Heterodera oryzicola* | — | see FIG. 10 | Rice (*Oryza sativa*) | |
| *Heterodera urticae* | 4 | Ireland and Bulgaria; presumably present throughout Europe | — | stinging nettle (*Urtica dioica*) and *U. urens* |
| *Globodera pallida* | 5 | see FIG. 7 | Potato (*Solanum tuberosum*) and many other *Solanum* species, incl. tomato (*Lycopersicon* spp.) | |
| *Globodera rostochiensis* | 5 | see FIG. 9 | idem as *G. pallida* | |
| *Globodera tabacum* | 5 | see FIG. 8 | Solanaceae, especially tobacco ((*Nicotiana tabacum*) and tomato (*Lycopersicon esculentum*) | |

TABLE 1-continued

Details of the subgenus-clusters of cyst nematodes proposed in the present invention.

| Species | Subgenus Cluster (FIG. 11) | Distribution | Host crop | Non-crop host |
|---|---|---|---|---|
| *Globodera achilleae* (syn: *Globodera millefolii*) | 6 | UK, The Netherlands, Germany, Slovak Republic, Slovenia, former Yugoslavia | — | yarrow (*Achillea millefolium*) |
| *Globodera artemisiae* | 6 | Sweden, Baltic States, Germany, The Netherlands, Russia and China | — | mugwort (*Artemisia vulgaris L.*) (*Compositae*: Anthemideae) |

TABLE 2

Details of the subgenus-clusters detection method proposed in the present invention.

Figure 6:
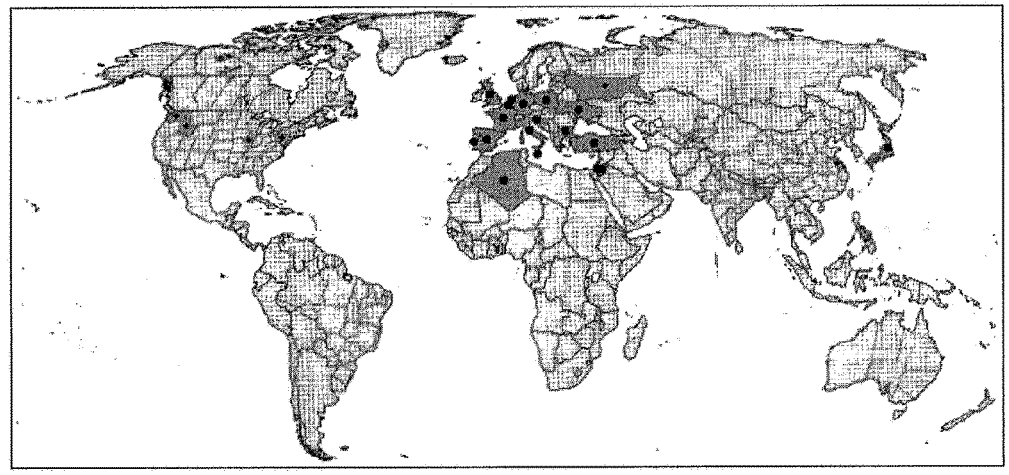
Figure 7:
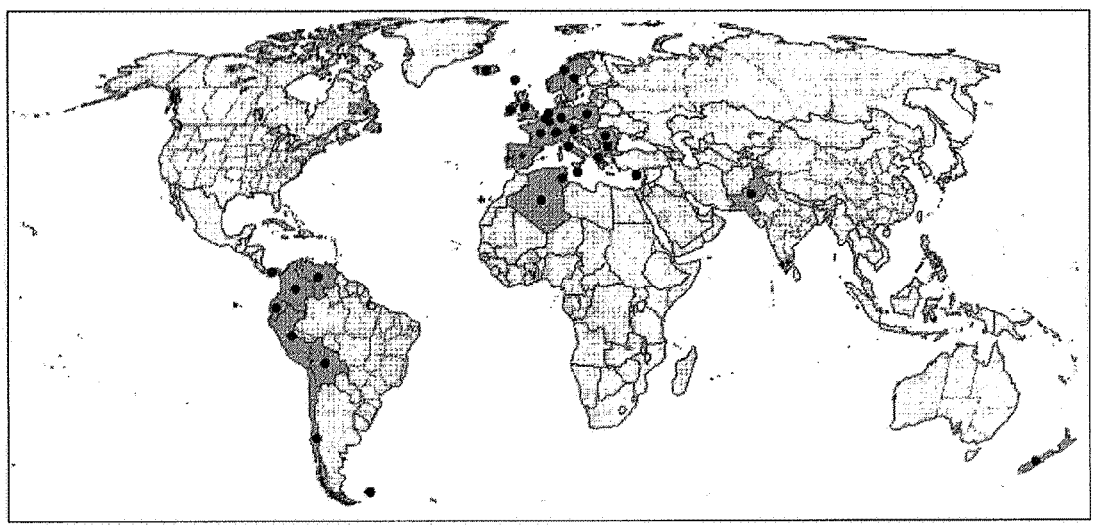
Figure 8:
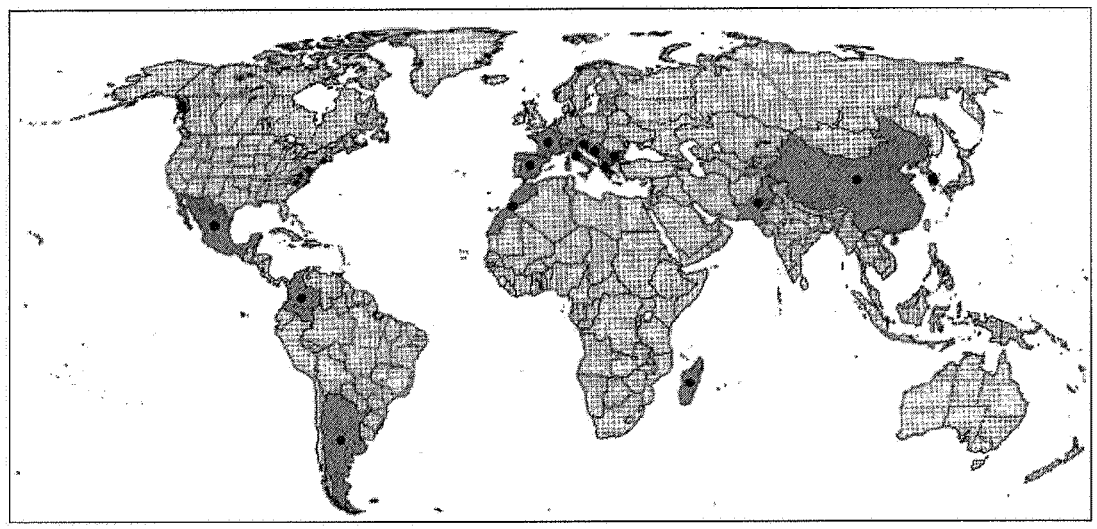
Figure 9:
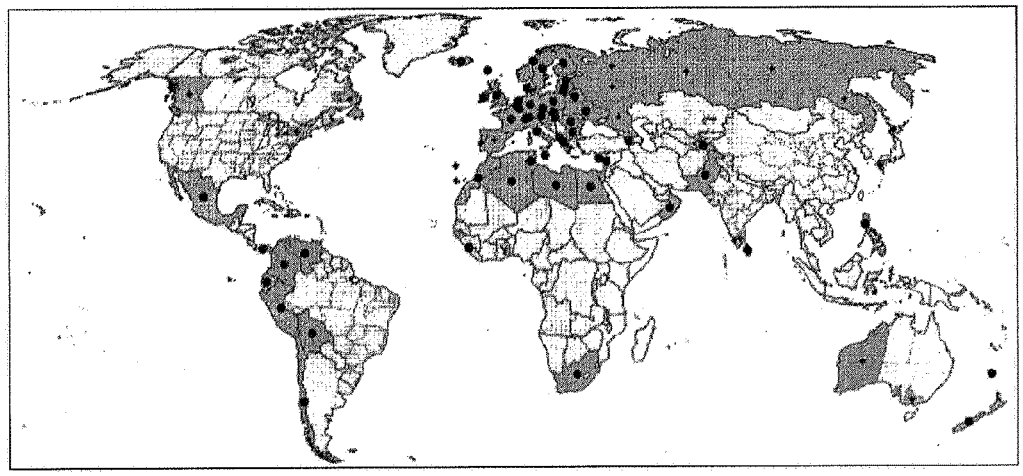
Figure 10:
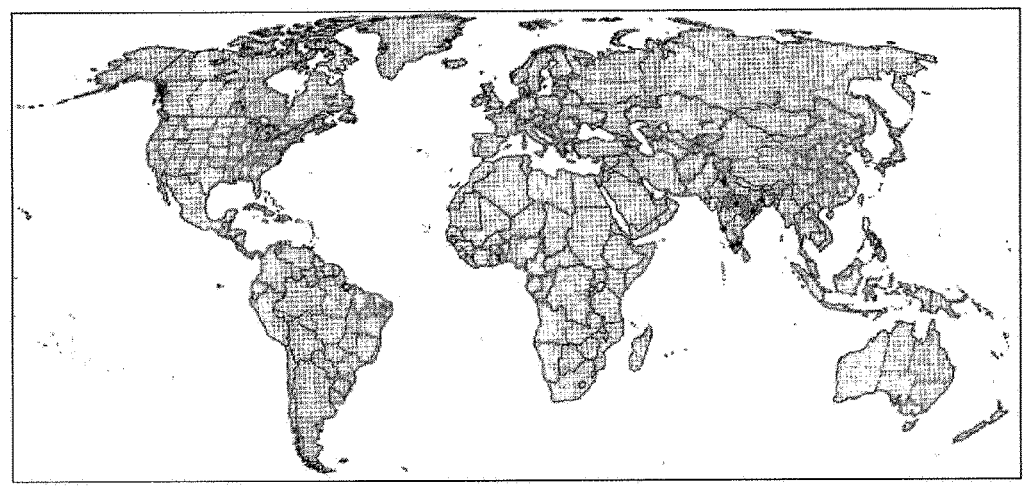

| Subgenus Cluster (FIG. 11) | Test sample (soil or cyst sample from field intended for growth of . . .) | Growing region | Positive signal Indicative of species |
|---|---|---|---|
| 1 | sugarbeet | see FIG. 1 | *Heterodera schachtii* |
|   |           | see FIG. 3 | *Heterodera trifolii/betae* |
|   | soybean   | see FIG. 2 | *Heterodera glycines* |
| 2 | corn (maize) | see FIG. 4 | *Heterodera zeae* |
| 3 | cereals   | see FIG. 5 | *Heterodera avenae/mani* |
| 4 | peas and beans | see FIG. 6 | *Heterodera goettingiana* |
| 5 | potato or tomato | see FIG. 7 | *Globodera pallida* |
|   |           | see FIG. 9 | *Globodera rostochiensis* |
|   | tobacco or tomato | see FIG. 8 | *Globodera tabacum* |

Example 2

LSU DNA-Based Identification of Potato Cyst Nematodes

The present Example illustrates the methods and products of the present invention. In this Example, species-specific pairs of hybridization primers targeting the large subunit ribosomal DNA were used to identify the nematodes *G. pallida* en *G. rostochiensis* in artificially prepared samples by q-PCR.

A series of samples was prepared by providing an aqueous suspension containing a defined number of cysts (0-4) of either *G. pallida* alone (sample nrs. 1-4), *G. rostochiensis* alone (sample nrs. 8-11) or combinations of different ratios of *G. pallida* en *G. rostochiensis* (sample nrs. 5-7).

TABLE 3

Artificial samples prepared for species-specific detection of potato cyst nematodes (see text for desription).

| Sample nr: | # *G. pallida* cysts | # *G. rostochiensis* cysts |
|---|---|---|
| 1 | 1 | 0 |
| 2 | 2 | 0 |
| 3 | 3 | 0 |
| 4 | 4 | 0 |
| 5 | 1 | 3 |
| 6 | 2 | 2 |
| 7 | 3 | 1 |
| 8 | 0 | 1 |
| 9 | 0 | 2 |

TABLE 3-continued

Artificial samples prepared for species-specific detection of potato cyst nematodes (see text for desription).

| Sample nr: | # *G. pallida* cysts | # *G. rostochiensis* cysts |
|---|---|---|
| 10 | 0 | 3 |
| 11 | 0 | 4 |

The samples were lysed, DNA was extracted from the cysts and used as template in a q-PCR reaction. Since the DNA content of a nematode cyst is highly variable, the quantitative DNA signal obtained from PCR amplification reflects the number of juveniles present in cysts, rather than the number of cyst per se.

The following primers were used:

```
primers for G. pallida:
Gp-forward: TGG GAT GGT GTT CAT TCT GC

Gp-reverse: CAA GCT CAT GCA GCT GTC primers for G. rostochiensis:
Gr-forward: GTG AGC TTG GAT TGG CCT Gr-reverse: CAA GCT CAT GCA GCT GCT
```

The primers were used in a standard nucleic acid amplification protocol with quantitative detection of signals obtained after each round of amplification (Q-PCR). *C. elegans* served as negative control. A DNA-sample of either *G. pallida* or *G. rostochiensis* served as positive control. The following amplification protocol was applied:

| 95° C. | 3 min | 1x |
| 95° C. | 10 sec | 50x |
| 62° C. | 1 min | |
| 72° C. | 20 sec | |

The results of the experiment are presented in the Tables below (Table 4 for *G. pallida* primers; Table 5 for *G. rostochiensis* primers; and Table 6 for *C. elegans*). In these tables, the number of cycles needed to obtain a relative fluorescense signal readout (RFU) above threshold level (RFU 102,42) is provided. A low cycle number (<25) indicates detection of amplified product in an early cycle.

TABLE 4

G. pallida Q-PCR

| 1 | 2 | 3 | 4 | 5 | 6 | 7 | 8 | 9 | 10 | 11 |
|---|---|---|---|---|---|---|---|---|---|---|
| 1pal | 2pal | 3pal | 4pal | 1pal-3ros | 2pal-2ros | 3pal-1ros | 1ros | 2ros | 3ros | 4ros |
| 18.09 | 19.69 | 17.89 | 17.38 | 18.63 | | 17.19 | 17.61 | N/A | 34.56 | N/A | N/A |
| NTC | Pos | | | | | | | | | |
| N/A | 17.32 | | | | | | | | | |

N/A = not detected above threshold value

TABLE 5

G. rostochiensis Q-PCR

| 1 | 2 | 3 | 4 | 5 | 6 | 7 | 8 | 9 | 10 | 11 |
|---|---|---|---|---|---|---|---|---|---|---|
| 1pal | 2pal | 3pal | 4pal | 1pal-3ros | 2pal-2ros | 3pal-1ros | 1ros | 2ros | 3ros | 4ros |
| N/A | N/A | N/A | N/A | 20.83 | 20.01 | 28.72 | 21.72 | 21.26 | 20.04 | 19.75 |
| NTC | Pos | | | | | | | | | |
| N/A | 23.78 | | | | | | | | | |

TABLE 6

C. elegans control

| 1 | 2 | 3 | 4 | 5 | 6 | 7 | 8 | 9 | 10 | 11 |
|---|---|---|---|---|---|---|---|---|---|---|
| 1pal | 2pal | 3pal | 4pal | 1pal-3ros | 2pal-2ros | 3pal-1ros | 1ros | 2ros | 3ros | 4ros |
| 24.70 | 24.04 | 23.97 | 24.08 | 23.88 | | 23.75 | 24.91 | 23.96 | 24.29 | 23.93 | 23.90 |
| NTC | Pos | | | | | | | | | |
| 35.63 | 16.26 | | | | | | | | | |

Amplification charts for the experiments are provided in FIG. 24A for *G. pallida* and FIG. 24B for *G. rostochiensis*.

---

The invention claimed is:

1. A method for determining the presence of a cyst nematode in a sample comprising the steps of:
providing a pair of bidirectional oligonucleotide primers or an oligonucleotide probe wherein each primer or the probe hybridizes specifically, under stringent hybridization conditions, to a coding region of a Large Subunit (LSU) ribosomal RNA (rRNA), or wherein each primer or the probe hybridizes specifically, under stringent hybridization conditions, to a coding region of the complement or transcript thereof, of all species in a subgenus-cluster of nematodes, said subgenus-cluster comprising cyst nematodes belonging to at least one species of nematode, and wherein said primers or probe do not hybridize to a coding region of a Large Subunit (LSU) ribosomal RNA (rRNA) or to a coding region of the complement or transcript thereof of cyst nematodes not part of said subgenus-cluster of cyst nematodes;
providing a sample in which the presence of the cyst nematode is to be detected; and
performing a nucleic acid detection assay on said sample using said pair of bidirectional oligonucleotide primers or said oligonucleotide probe.

2. The method according to claim 1, wherein said subgenus-cluster comprises cyst nematodes belonging to at least two species of nematodes.

3. The method according to claim 1, wherein said cyst nematode is a nematode belonging to the family Heteroderidae.

4. The method according to claim 1, wherein said sample is selected from a soil sample, a root or tuber sample, a sample of soil attached to roots, a sediment sample and a sludge sample.

5. The method according to claim 1, wherein said sample is a sample of cysts isolated from a soil, root or tuber, sediment or sludge sample.

6. The method according to claim 1, wherein said sample represents a mixed population comprising cysts of multiple species of nematodes.

7. The method according to claim 1, wherein said subgenus-cluster comprises cyst nematodes belonging to at least one species selected from the group consisting of *Heterodera schachtii, Heterodera glycines, Heterodera trifolii, Heterodera betae, Heterodera zeae, Heterodera litoralis, Heterodera avenae, Heterodera aucklandia, Heterodera mani, Heterodera goettingiana, Heterodera urticae, Globodera pallida, Globodera rostochiensis, Globodera tabacum, Globodera achilleae, Globodera millefolii,* and *Globodera artemisiae.*

8. The method according to claim 1, wherein said subgenus-cluster is selected from the following clusters:
1) The subgenus cluster consisting of the species *Heterodera schachtii, Heterodera glycines, Heterodera trifolii* and *Heterodera betae;*
2) The subgenus cluster consisting of the species *Heterodera zeae* and *Heterodera litoralis;*
3) The subgenus cluster consisting of the species *Heterodera avenae, Heterodera aucklandia* and *Heterodera mani;*
4) The subgenus cluster consisting of the species *Heterodera goettingiana* and *Heterodera urticae;*
5) The subgenus cluster consisting of the species *Globodera pallida, Globodera rostochiensis* and *Globodera tabacum;* and
6) The subgenus cluster consisting of the species *Globodera achilleae, Globodera millefolii* and *Globodera artemisiae.*

9. The method according to claim 1, wherein said detection assay comprises isolating nucleic acids from said sample or from said cysts and performing a nucleic acid amplification reaction using said pair of bidirectional primers.

10. A method for determining the presence of cyst nematode in a sample comprising the steps of:
providing a first pair of bidirectional oligonucleotide primers or an oligonucleotide probe wherein each primer or the probe hybridizes specifically, under stringent hybridization conditions, to a coding region of the Large Subunit (LSU) ribosomal RNA (rRNA), or wherein each primer or the probe hybridizes specifically, under stringent hybridization conditions to a coding region of the complement or transcript thereof, of all species in a subgenus-cluster of nematodes, said subgenus-cluster comprising cyst nematodes belonging to at least two species of nematodes, and wherein said primers or oligonucleotide probe do not hybridize to a coding region of the Large Subunit (LSU) ribosomal RNA (rRNA), or the coding region of the complement or transcript thereof, of cyst nematodes that do not belong to said subgenus-cluster of cyst nematodes;
providing a sample in which the presence of the cyst nematode is to be detected;
performing a first nucleic acid detection assay on said sample using said first pair of bidirectional oligonucleotide primers or said oligonucleotide probe;
providing a second pair of bidirectional oligonucleotide primers or an oligonucleotide probe that hybridizes specifically, under stringent hybridization conditions, to a nucleic acid sequence encoding a Small Subunit (SSU) or Large Subunit (LSU) ribosomal RNA (rRNA), or the complement or transcript thereof, of a single nematode species, and wherein said primers or oligonucleotide probe do not hybridize to a nucleic acid sequence encoding a Small Subunit (SSU) or Large Subunit (LSU) ribosomal RNA (rRNA), or the complement or transcript thereof, of other species of cyst nematodes; and
performing a second nucleic acid detection assay on said same sample using said second pair of bidirectional oligonucleotide primers or said oligonucleotide probe.

11. The method according to claim 10, wherein said subgenus-cluster is selected from the following clusters:
1) the subgenus cluster consisting of the species *Heterodera schachtii, Heterodera glycines, Heterodera trifolii* and *Heterodera betae;*
2) the subgenus cluster consisting of the species *Heterodera zeae* and *Heterodera litoralis;*
3) the subgenus cluster consisting of the species *Heterodera avenae, Heterodera aucklandia* and *Heterodera mani;*
4) the subgenus cluster consisting of the species *Heterodera goettingiana* and *Heterodera urticae;*
5) the subgenus cluster consisting of the species *Globodera pallida, Globodera rostochiensis* and *Globodera tabacum;* and
6) the subgenus cluster consisting of the species *Globodera achilleae, Globodera millefolii* and *Globodera artemisiae.*

12. The method according to claim 10, wherein said single nematode species is selected from the group consisting of *Heterodera schachtii, Heterodera glycines, Heterodera trifolii, Heterodera betae, Heterodera zeae, Heterodera litoralis, Heterodera avenae, Heterodera aucklandia, Heterodera mani, Heterodera goettingiana, Heterodera urticae, Globodera pallida, Globodera rostochiensis, Globodera tabacum, Globodera achilleae, Globodera millefolii,* and *Globodera artemisiae.*

* * * * *